(12) United States Patent
Falci

(10) Patent No.: US 7,130,691 B2
(45) Date of Patent: Oct. 31, 2006

(54) METHOD FOR ERADICATING PAIN OF CENTRAL ORIGIN RESULTING FROM SPINAL CORD INJURY

(76) Inventor: Scott P. Falci, 4241 S. Allison St., Lakewood, CO (US) 80235

( * ) Notice: Subject to any disclaimer, the term of this patent is extended or adjusted under 35 U.S.C. 154(b) by 354 days.

(21) Appl. No.: 10/232,908

(22) Filed: Aug. 30, 2002

(65) Prior Publication Data
US 2004/0006376 A1    Jan. 8, 2004

Related U.S. Application Data

(60) Provisional application No. 60/392,396, filed on Jun. 27, 2002.

(51) Int. Cl.
*A61N 1/18* (2006.01)

(52) U.S. Cl. .................................................. 607/46

(58) Field of Classification Search ............ 607/46; 435/6; 530/350
See application file for complete search history.

(56) References Cited

U.S. PATENT DOCUMENTS

| | | | | |
|---|---|---|---|---|
| 3,822,708 A * | 7/1974 | Zilber | ........................ | 607/46 |
| 5,330,515 A * | 7/1994 | Rutecki et al. | ............... | 607/46 |
| 5,755,750 A | 5/1998 | Petruska et al. | | |
| 5,806,522 A * | 9/1998 | Katims | ........................ | 600/554 |
| 5,844,097 A * | 12/1998 | Cameron et al. | ........ | 530/388.2 |
| 5,938,690 A * | 8/1999 | Law et al. | ..................... | 607/46 |
| 6,002,964 A * | 12/1999 | Feler et al. | .................... | 607/46 |
| 6,018,675 A | 1/2000 | Apkarian et al. | | |
| 6,421,566 B1 * | 7/2002 | Holsheimer | .................. | 607/46 |
| 6,573,067 B1 * | 6/2003 | Dib-Hajj et al. | ........... | 435/69.1 |

OTHER PUBLICATIONS

Nashold, Jr., Blaine S., Ostdahl, Roger H., Bullitt, Elizabeth, Friedman, Allan, and Brophy, Brian, "Dorsal Root Entry Zone Lesions: A New Neurosurgical Theraphy for Deafferentation Pain", *Advances in Pain Research and Therapy*, 1983, vol. 5, pp. 739-750.
Eide, P.K., "Pathophysiological Mechanisms of Central Neuropathic Pain After Spinal Cord Injury", *Scientific Review* 1998, 36, 601-612.
Siddall, P.J., Loeser, J.D., "Pain Following Spinal Cord Injury", *Scientific Review* 2001, 39, 63-73.
Alpantaki, et al., "Sympathetic and Sensory Neural Elements in the Tendon of the Long Head of the Biceps," *The Journal of Bone and Joint Surgery*, Jul. 2005, pp. 1580-1583, vol. 87-A, No. 7.
Browder, "Do Sympathetic Nerves Transmit Painful Impulses?", *The American Journal of Surgery*, 1932, pp. 100-102, vol. 18, No. 1.

(Continued)

*Primary Examiner*—George Manuel
*Assistant Examiner*—Lenwood Faulcon, Jr.
(74) *Attorney, Agent, or Firm*—Dorsey & Whitney LLP

(57) ABSTRACT

Methods are provided to reliably identify and surgically eradicate aberrant DREZ in patients suffering from spinal cord injury. The methods include identifying potential aberrant DREZ using a combination of mapping techniques based on the location of the patients perceived pain, analysis of the spontaneous electrical hyperactivity in targeted DREZ, and analysis of evoked transcutaneous C-fiber stimulation both in pre-operative and operative conditions. Methods are also provided for identifying potential pain effecters in aberrant DREZ, useful in the preparation of non-invasive therapeutics for central pain characteristic of spinal cord injury.

2 Claims, 12 Drawing Sheets

OTHER PUBLICATIONS

Cronin, et al., "Laminar distribution of $GABA_A$-and glycine-receptor mediated tonic inhibition in the dorsal horn of the rat lumbar spinal cord: effects of picrotoxin and strychnine on expression of Fos-like immunoreactivity," *Pain*, Nov. 2004, pp. 156-163, vol. 112.

Davis, "Pain and Suffering Following Spinal Cord Injury," *Clinical Orthopaedics and Related Research*, 1975, pp. 76-80, No. 112.

DeLeo, et al., "The role of neuroinflammation and neuroimmune activation in persistent pain," *Pain*, 2001, pp. 1-6, vol. 90.

Deutscher [editor], *Methods in Enzymology*, 1990, vol. 182: *Guide to Protein Purification*, Academic Press, Inc.

Dotson, Clinical Neurophysiology Laboratory Tests to assess the Nociceptive System in Humans, *Journal of Clinical Neurophysiology*, 1997, pp. 32-45, vol. 14, No. 1.

Echlin, "Pain Responses on Stimulation of the Lumbar Sympathetic Chain under Local Anesthesia," *Journal of Neurosurgery*, 1949, pp. 530-533, vol. 6.

Eide, "Pathophysiological mechanisms of central neuropathic pain after spinal cord injury," *Spinal Cord*, 1998, pp. 601-612, vol. 36, No. 9.

Freeman, et al., "Surgical Relief of Pain in Paraplegic Patients," *Archives of Surgery*, 1947, pp. 433-440, vol. 55.

Friedman et al., "DREZ lesions for relief of pain related to spinal cord injury," *Journal of Neurosurgery*, 1986, pp. 465-469, vol. 65, No. 4.

Goeddel [editor], *Methods in Enzymology*, 1990, vol. 185: *Gene Expression Technology*, Academic Press, Inc.

Graham, et al., "Chapter 11: Manipulation of Adenoviris Vectors," *Methods in Molecular Biology*, 1991, pp. 109-128, vol. 7: Gene Transfer and Expression Protocols, The Humana Press Inc., Clifton, New Jersey.

Hains, et al., "Changes in electrophysiological properties and sodium channel $Na_v1.3$ expression in thalamic neurons after spinal cord injury," *Brain*, 2005, pp. 2359-2371, vol. 128.

Harris, "The Role of the Sympathetic in Sensory Conduction and Certain Neuralgias," *British Medical Journal*, 1936, pp. 112-115, vol. 2.

Harvey, et al., "GlyR α3: An Essential Target for Spinal $PGE_2$-Mediated Inflammatory Pain Sensitization," *Science*, 2004, pp. 884-887, vol. 304.

Human, "Research knocks out pain," *Denver Post*, 2005.

Innis, et al., [editor], *PCR Protocols: A Guide to Methods and Applications*, 1990, Academic Press, Inc., San Diego, California.

Ishijima, et al., "Lesions of Spinal and Trigeminal Dorsal Root Entry Zone for Deafferentation Pain," *Applied Neurophysiology*, 1988, pp. 175-187, vol. 51, No. 2-5.

Ji, "Peripheral and Central Mechanisms of Inflammatory Pain, with Emphasis on MAP Kinases," *Current Drug Targets —Inflammation & Allergy*, 2004, pp. 299-303, vol. 3, No. 3.

Jongen, et al., "Intrathecal injection of GDNF and BDNF induces immediate early gene expression in rat spinal dorsal horn," *Experimental Neurology*, Jul. 2005, pp. 255-266, vol. 194, No. 1.

Katims, et al. "Transcutaneous Nerve Stimulation," *Applied Neurophysiology*, 1986, pp. 86-91, vol. 49, No. 1-2.

Li, et al., "Alterations in Spinal Cord Gene Expression After Hindpaw Formalin Injection," *Journal of Neuroscience Research*, 2004, pp. 533-541, vol. 78.

Liu, et al., "Peripherally Delivered Glutamic Acid Decarboxylase Gene Therapy for Spinal Cord Injury Pain," *Molecular Therapy*, 2004 pp. 57-66, vol. 10, No. 1.

Marx, "Prolonging the Agony," *Science*, 2004, pp. 326-329, vol. 305.

Melzack, et al., "Phantom Body Pain in Paraplegics: Evidence for a Central 'Pattern Generating Mechanism' for Pain," *Pain*, 1978, pp. 195-210, vol. 4.

Miller, "The Dark Side of Glia" *Science*, 2005, pp. 778-781, vol. 308.

Morales-Aza, et al., "Inflammation alters cation chloride cotransporter expression in sensory neurons," *Neurobiology of Disease*, 2004, pp. 62-69, vol. 17.

Nashold Jr., et al., "Dorsal root entry zone lesions for pain relief," *Journal of Neurosurgery*, 1979, pp. 59-69, vol. 51, Nos. 1-6.

Nashold Jr., et al., "Dorsal root entry zone lesions to control central pain in paraplegics," *Journal of Neurosurgery*, 1981, pp. 414-419, vol. 55, Nos. 1-6.

Nesic, et al., "Transcriptional profiling of spinal cord injury-induced central neuropathic pain," *Journal of Neurochemistry*, 2005, pp. 998-1014, vol. 95.

Okuda-Ashitaka, et al., "Nocistatin, a peptide that blocks nociceptin action in pain transmission," *Nature*, 1998, pp. 286-289, vol. 392, No. 6673.

Ossipov, et al., "Spinal and Supraspinal Mechanisms of Neuropathic Pain," *Annals of the New York Academy of Sciences*, 2000, pp. 12-24, vol. 909.

Patte-Mensah, et al., "Impact of neuropathic pain on the gene expression and activity of cytochrome P450side-chain-cleavage in sensory neural networks," *Cellular and Molecular Life Sciences*, Sep. 2004, pp. 2274-2284, vol. 61, No. 17.

Pick, *The Autonomic Nervous System*, 1970, J.B. Lippincott Company, U.S.

Rath, et al., "Results of DREZ Coagulations for Pain Related to Plexus Lesions, Spinal Cord Injuries and Postherpetic Neuralgia," *Acta Neurochirurgica*, 1996, pp. 364-369, vol. 138, No. 4.

Rath, et al., "DREZ Coagulations for Deafferentation Pain Related to Spinal and Peripheral Nerve Lesions: Indication and Results of 79 Consecutive Procedures," *Stereotactic and Functional Neurosurgery*, 1997, pp. 161-167, vol. 68.

Richards, et al., "Psycho-Social Aspects of Chronic Pain in Spinal Cord Injury," *Pain*, 1980, pp. 355-366, vol. 8.

Salter, "Cellular Signalling Pathways of Spinal Pain Neuroplasticity as Targets for Analgesic Development," *Current Topics in Medicinal Chemistry*, 2005, pp. 557-567, vol. 5, No. 6.

Sambrook, et al., *Molecular Cloning*, 1989, Cold Spring Harbor Laboratory Press, U.S.

Schmidt, et al., "Innervation Territories of Mechanically Activated C Nociceptor Units in Human Skin," *Journal of Neurophysiology*, 1997, pp. 2641-2648,vol. 78, No. 5.

Shields, "Functional Anatomy of the Autonomic Nervous System," *Journal of Clinical Neurophysiology*, 1993, pp. 2-13, vol. 10, No. 1.

Siddal, et al., "Pain following spinal cord injury," *Spinal Cord*, 2001, pp. 63-73, vol. 39, No. 2.

Song, et al., "Activation of ERK/CREB pathway in spinal cord contributes to chronic constrictive injury-induced neuropathic pain in rats," *Acta Pharmacologica Sinica*, Jul. 2005, pp. 789-798, vol. 26, No. 7.

Spataro, et al., "Spinal Gap Junctions: Potential Involvement in Pain Facilitation," *The Journal of Pain*, Sep. 2004, pp. 392-405, vol. 5, No. 7.

Störmer, et al., "Chronic pain/dysaesthesiae in spinal cord injury patients: results of a multicentre study," *Spinal Cord*, 1997, pp. 446-455, vol. 35, No. 7.

Vierck Jr., et al., "Pain following spinal cord injury: animal models and mechanistic studies," *Pain*, 2000, pp. 1-5, vol. 89.

Wieseler-Frank, et al., "Central Proinflammatory Cytokines and Pain Enhancement," *Neurosignals*, 2005, pp. 166-174, vol. 14.

Woolsey, "Chronic Pain Following Spinal Cord Injury," *The Joural of the American Paraplegia Society*, 1986, pp. 39-41, vol. 9.

Yokota, et al., "Sympathetic Skin Response in Patients with Multiple Sclerosis Compared with Patients with Spinal Cord Transection and Normal Controls," *Brain*, 1991, pp. 1381-1394, vol. 114, No. 3.

Yu, et al., "Activation of the ERK1/2 signaling cascade by excitotoxic spinal cord injury," *Molecular Brain Research*, 2005, pp. 244-255, vol. 138.

Yezierski, "Pain following spinal cord injury: the clinical problem and experimental studies," *Pain*, 1996, pp. 185-194, vol. 68, Nos. 2-3.

\* cited by examiner

METHOD FOR ERADICATING PAIN OF CENTRAL ORIGIN RESULTING FROM SPINAL CORD INJURY

CROSS REFERENCE TO RELATED APPLICATIONS

This application claims priority to U.S. Provisional Patent application Ser. No. 60/392,396, filed on Jun. 27, 2002, and entitled METHOD FOR ERADICATING PAIN RESULTING FROM SPINAL CORD INJURY.

FIELD OF THE INVENTION

The invention generally relates to eradicating pain following spinal cord injury. More specifically, the invention provides methods for identifying dorsal root entry zones (DREZs) involved in generating and/or communicating a pain signal(s) associated with spinal cord injury, and to modifying the identified DREZ(s) so as to minimize the pain associated with the spinal cord injury. In addition, the invention provides procedures for identifying targets within the pain associated DREZs that can be used in the development of non-invasive therapies for the treatment of pain resulting from spinal cord injury.

BACKGROUND OF THE INVENTION

Severe or disabling pain is a frequent result from spinal cord injury (SCI). Pain often occurs within weeks or months of the spinal cord injury, and typically persists or even intensifies with time. Over the past half century, studies have illustrated that patients suffering a SCI suffer anywhere from between 20 and 77% incidence of some level of severe or disabling chronic pain. Davis et al., *Clin Orthop* 112:76–80 (1975); Richards et al., *Pain* 8:355–366 (1980); Siddall et al., Spinal Cord 39:63–73 (2001); Stormer et al., *Spinal Cord* 446–455 (1997); Woolsey, *J Am Paraplegia* 9:39–41 (1986). It has also been well documented that patients suffering from at least some level of severe or disabling chronic pain show reduced rehabilitation potential and tend to have a significant overall reduction in quality of life. As such, severe or disabling chronic pain, incident from SCI, is a major concern for patients with SCI, is a major concern within the health care industry, and is a major concern within society in general.

Patients suffering from SCI have pain(s) that originate in the central nervous system, often termed central pain, and includes pain defined as central deafferentation pain. Eide, *Spinal Cord* 36:601–612 (1998); Ishijima et al., *Appl Neurophysiol* 51:2–5, 175–187 (1988); Melzack et al., *Pain* 4:195–210 (1978); Yezierski, *Pain* 68:185–194 (1996). Central deafferentation pains are believed to involve the abnormal up-regulation of neuronal activity after nerve injury. Electrophysiological studies have suggested that SCI causes abnormal changes in the firing pattern of neurons which signal pain sensation, including increased spontaneous activity of the neurons, reduced neuron thresholds, increased responsiveness to peripheral stimulation (hyperexcitability), prolonged after-discharges to repetitive stimulation, and the expansion of the peripheral receptive fields of central neurons. Eide, *Spinal Cord* 36:601–612 (1998).

Central pain has proven notoriously difficult to treat, often proving recalcitrant to modern medical and surgical pain treatment procedures. Of particular therapeutic significance, is the surgical treatment of specific dorsal root entry zone(s) (DREZ(s)) of the spinal cord. Surgical treatment of a central pain generating DREZ at the level of an injury is believed to disrupt the neural, i.e., electrical, communication and/or generation of aberrant pain signals that result from the injury. Initially, empiric techniques have been used to target DREZ sites for surgical treatment, resulting in modest outcomes for the patient, i.e., DREZ sites at the site of injury targeted for treatment. Friedman et al., *J Neurosurg* 65:465–469 (1986); Ishijima et al., *Appl Neurophysiol* 51:2–5, 175–187 (1988); Rath et al., *Acta Neurochir* 138:4, 364–369 (1996); Rath et al., *Sterotact Funct Neurosurg* 68:1–4, Pt 1, 161–167 (1997). One of the more relevant patient studies using this empirical technique suggests that approximately 50% of patients so treated achieve good relief from SCI associated pain. Friedman et al., *J Neurosurg* 65:465–469 (1986). In that series, at-level pain, i.e., pain at the immediate vicinity of the injury, responded best (74% "good results") and below-level pain, i.e., pain below the level of injury, responded poorly (20% "good results"). These results suggest that empiric DREZ lesioning techniques can provide satisfactory relief for about half the number of patients treated, especially if the patient is suffering from pain in the vicinity of the injury. However, the results also suggest that a significant number of patients do not receive benefit from the technique, especially where the patient is suffering from pain perceived below the level of the injury.

More recently, a single study on patients suffering from SCI found that when intramedullary recordings of spontaneous neuroelectric hyperactivity were used to direct DREZ lesioning, substantially better outcomes were attained. Edgar et al., *J Spinal Dis* 6:48–56 (1993). This more targeted DREZ identification technique provides evidence that neuroelectrical targeting techniques could provide better outcomes for eradicating SCI based pain. Against this backdrop the present invention has been developed.

BRIEF SUMMARY OF THE INVENTION

The present invention provides a somatotopic map that correlates the perceived pain in a patient to a potentially aberrant DREZ in the patient. The map is prepared using the methods of the present invention, which include comparing the perceived pain in a series of patients with the measured neuroelectrical activity of DREZ and thereby correlating perceived pain with aberrant DREZ location. The data from patients with spinal cord injuries is accumulated to provide a standardized map having the typical pattern of the DREZ which are responsible for perceived pain in a patient with a spinal cord injury.

The present invention further provides methods for minimizing central pain in a patient having a spinal cord injury. The method includes determining the level of the injury to the spinal cord in the patient, typically through examination; determining the location of perceived pain in the patient; and mapping the location of the perceived pain in the patient to a pain generating DREZ of the patient's spinal cord, the mapping consistent with a pre-determined somatotopic map. Note that the somatotopic map provides a guide for where a perceived pain correlates to a DREZ location, as the map has been previously prepared from a series of test subjects having spinal cord injuries. The methods of the present invention further provide for the surgical exposure of the somatotopically identified DREZ, and the introduction of one or more lesions in the identified pain generating DREZ, wherein the one or more lesions minimizes central pain in the patient.

The methods for minimizing central pain in a patient having a spinal cord injury further include: confirming that the somatotopically mapped location of aberrant DREZ in a patient with a spinal cord injury have aberrant neuroelectrical activity through a combination of spontaneous electrophysiologic analysis and/or transcutaneous C-fiber stimulation.

Finally, methods of the present invention provide for the identification of pain effecters in aberrant DREZ responsible for some or all of the pain perceived by a patient with a spinal cord injury.

These and various other features and advantages of the invention will be apparent from a reading of the following detailed description and review of the appended claims.

DETAILED DESCRIPTION OF THE INVENTION

Figure 1:
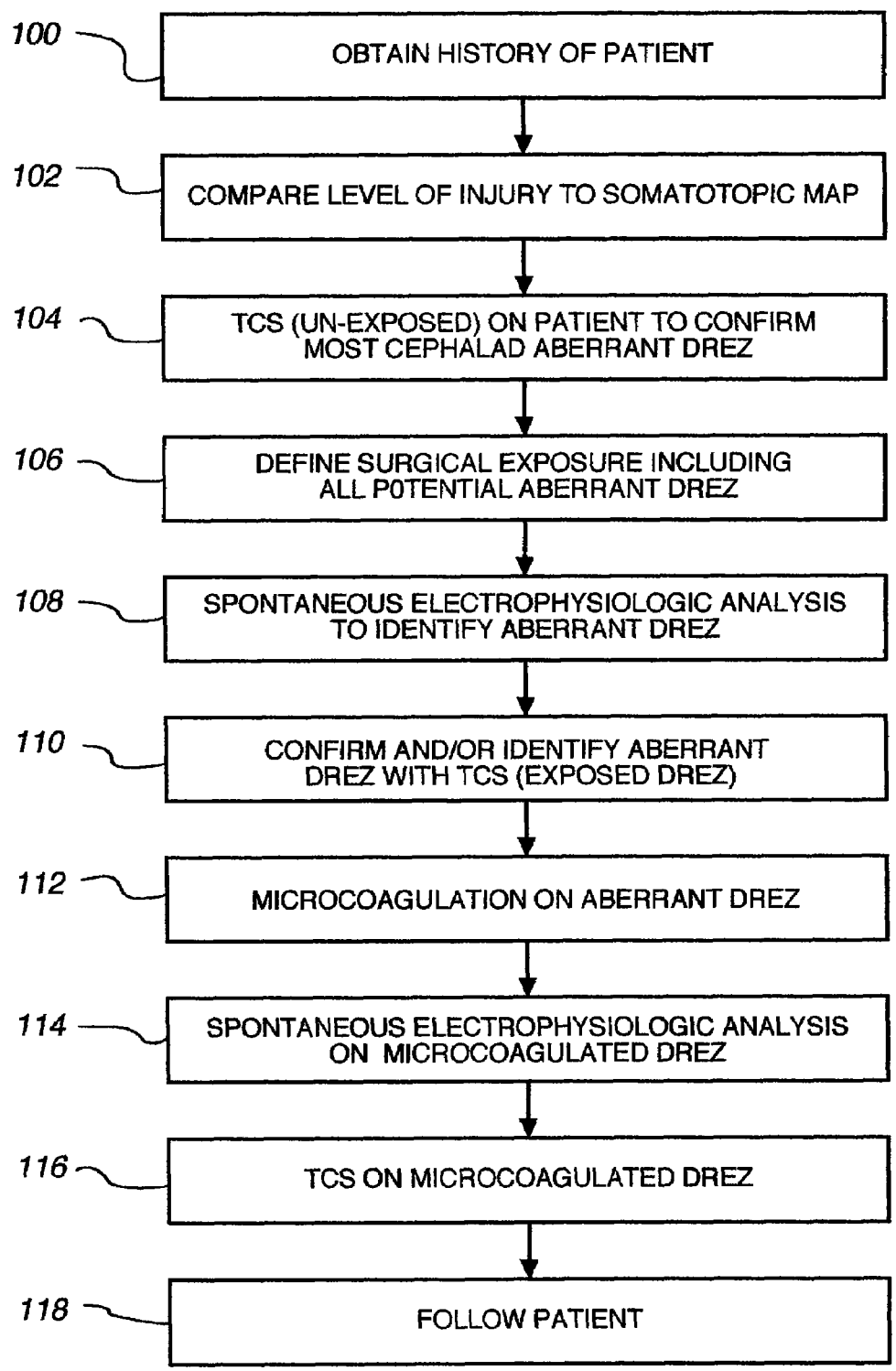
FIG. 1 is a flow diagram of a method for identifying aberrant DREZ(s) in a patient suffering from SCI in accordance with the present invention.

Definitions:

The following definitions are provided to facilitate understanding of certain terms used frequently herein and are not meant to limit the scope of the present disclosure.

"Dorsal root entry zone" (DREZ) refers to the area of the dorsal gray matter of the spinal cord in the region of the dorsal roots for a particular region of the spinal cord. For purposes of the present invention, a DREZ includes any portion of the entry zone area from the dorsal surface of the spinal cord where the roots enter to a depth of at least laminas V and VI. Note that some variation exists in the structure of a particular DREZ dependent on the region of the spine through which it passes, such variations are well known to those of skill in the art, and are within the scope of the present invention. Also note that there is a right and left DREZ at each region of the spinal cord, and that unless specified, the term DREZ treats the right and left DREZ interchangeably. In addition, the electrical activity in the left and right DREZ at a particular level do not necessarily have to be symmetrical, i.e., one side may show aberrant neuroelectric activity and the other shown normal neuroelectric activity.

"DREZ microcoagulation" refers to a modified surgical technique of the technique described by Nashold et al, *J Neurosurg*. 55:414–419 (1981) and Nashold et al., *J Neurosurg*. 51:59–69 (1979). Briefly, the principle of the technique is to destroy a target dorsal root entry zone area (see below how DREZs are targeted), using a fine electrode, or other like instrument. The area of destruction extends from the dorsal surface of the spinal cord where the root enters, to a depth of approximately 2 mm. The electrode is introduced for a distance of approximately 2 mm into the intermediolateral sulcus on the dorsal surface of the spinal cord. The direction of the electrode should be in the lateral medial plane with an angle of approximately 35° to 45°, although the angle of the recording electrode may vary dependent on the electrical data, and the 35° to 45° is provided as a point of reference. The level of current and period of time is known in the art. A temperature of approximately 90° is attained, although slightly lower temperatures are envisioned to be within the scope of the present invention.

"Minimizing pain" refers to any decrease in the level of perceived pain a patient feels as a result of the methods of the present invention.

"At-level pain" refers to pain that is perceived to occur at the level of injury to the spinal cord. Note also that for purposes of the present invention, a level is equivalent to a vertebrae within the spine and its corresponding spinal cord level.

"Below-level pain" refers to pain that is perceived to occur at least one level or more below the site of injury to the spinal cord.

"Pain generating DREZ" refers to any DREZ involved in the aberrant generation or communication of pain signals resultant from a SCI. Typically, a pain generating DREZ, as compared to a non-pain generating DREZ, involves neuronal hyperactivity and/or hyperexcitability that can be measured/identified in accordance with the techniques of the present invention, i.e., also referred to as a "hot" DREZ.

"Transcutaneous C-fiber stimulation (TCS)", or in a broader sense transcutaneous electrical nerve stimulation (TNS), refers to a technique that utilizes relatively non-painful current intensities having a frequency (preferably approximately 5 Hz) and waveform, to evoke C-fibers, including polymodal and sympathetic C-fibers, to identify neuroelectrical hyperactivity. The technique incorporates the use of an alternating current transcutaneous electrical nerve stimulator, for example a Neurometer CPT device (Neurotron, Inc., Baltimore, Md). The technique in this mode is performed on the exposed DREZ during the surgical lesioning procedure. TCS also refers to the technique of stimulating dermatomes in a patient pre-operatively with increasing current to identify potential pain inducing DREZ (as reported by the patient and in some instances confirmed by a SCI therapist). The technique in this mode provides information as to the most cephalad aberrant DREZ, but as expected, cannot provide information from the patient regarding DREZ below the site of injury.

"Pain effecters" refers to components of a neuron or neuronal support cell involved in the aberrant or pathologic generation or communication of central pain in a patient suffering a SCI. Potential pain effecters, for purposes of the present invention, are located in or communicate with the neurons of the DREZs identified using the methods of the present invention, and may include receptors, ion channels, transcription factors, neurotransmitters, and the like, as well as relevant nucleic acid molecules, e.g., RNA and DNA, involved in the transcription and translation of the receptors, ion channels, transcription factors, neurotransmitters, and the like.

Spinal Cord Injury and DREZs:

All vertebrate animals have a central axis of the body that consists of the spinal or vertebral column. The vertebral column consists of a number of connected irregular bones, termed the vertebrae, which surround and thereby protect a spinal cord. The vertebrae also support the weight of the trunk and transmit the weight to the lower limbs.

The vertebrae are grouped according to the region in which they lie—cervical, thoracic, lumbar, sacral and coccygeal or caudal. Each vertebrae has a ventral and dorsal side. In series with each vertebrae are a number of spinal nerves. Each nerve is formed by the union of an anterior (motor) and posterior (sensory) nerve-root. The posterior or dorsal nerve-roots are the central branches of the axons of the unipolar cells of the spinal ganglia. There are thirty-one pairs of spinal nerves: 8 cervical, 12 thoracic, 5 lumbar, 5 sacral and 1 coccygeal.

Injury to nerves often results in persistent pain. Often this pain is described as severe, diffuse and continuous with periods of exacerbation. It is widely accepted that injury to a nerve often results in the abnormal up-regulation of neuronal activity and that this up-regulation plays a key role in pain associated with the injury. Several electrophysiological studies have suggested that damaged nerves show abnormal changes in their firing pattern, including spontaneous activity, reduced thresholds and increased responsiveness to peripheral stimulation. Eide, *Spinal Cord,* 36:601–612 (1998).

The present invention provides methods that show that a combination of intramedullary electrical guidance techniques can be used to reliably identify aberrant pain generating DREZs, and that these methods can reliably identified pain generating DREZs at or above the level of injury, and surprisingly, identify DREZs that mediate below the level of injury pain. These methods provide aberrant DREZ identification and eradication techniques that are more reliable and effective than prior art techniques.

Directed DREZ Recording Techniques Performed on Exposed DREZ

The present invention utilizes a combination of two DREZ recording techniques to reliably identify pain generating DREZ in an exposed spine. The first technique involves measuring the spontaneous neuroelectrical activity of DREZ in a patient with SCI. The spinal cord of the patient is exposed in agreement with the patients history and the determination of potential aberrant DREZ with the somatotopic map of the present invention (see below). Note that the spinal levels are determined by an intraoperative radiography evaluation, and the injury site was identified using intraoperative ultrasonography. The dura mater of the spinal cord is opened and DREZ of the segments identified. Electrophysiological analysis of the DREZs are performed, starting with the DREZ at the level of injury and all levels cephalad until approximately four non-aberrant DREZs are identified. Note that if the somatotopic map suggest the potential for aberrant DREZ caudal to the level of injury in the patient, the electrophysiological analysis is performed as such (caudal) (see below)

Spontaneous neuroelectrical activity is measured by inserting an active electrode into a specific DREZ, wherein the active electrode is a 25 mm monopolar electrode, for example a MF 25 TECA Corporation, Pleasantville, N.Y. Approximately the distal 2 mm of the electrode is exposed. The electrode is inserted "free hand" in the DREZ with use of the intraoperative microscope at a depth of approximately 2 mm. The axis of implantation is approximately about 35 to 45° medially and is the same axis as used for the DREZ microcoagulation. Ground and reference glass subdermal electroencephalographic electrodes were placed in exposed paraspinous muscle bilaterally. Spontaneous electrophysiologic recordings are obtained using an evoked potential averager (Spectrum 32, Cadwell Laboratories, Kennewick Wash.) at a gain setting of approximately 50 with the high-frequency filter set at approximately 3 KHz and the low-frequency filter at 100 Hz. The recordings were approximately 1 second in duration, although other lengths of time are envisioned.

In a preferred embodiment, the recordings are analyzed by root mean square (RMS) (expressed in micro volts), frequency and voltage in the waveform by fast Fourier transform (FFT), and area under the waveform curve (expressed in micro volts per millisecond). In a preferred embodiment the analysis is performed by a subroutine in the Cadwell Spectrum 32 software, although other software applications are envisioned to be within the scope of the present invention.

In another embodiment, the initial data is passed through a tight digital filter with a band pass of 65 to 100 Hz. The data is then examined for "spindle bursts" in the one-second recording time.

Data from a target DREZ is interpreted by activity, where activities showing lower voltage and frequencies, i.e., from 4.5 µV to 6.5 µV, and preferably from 5 µV to 6 µV, and smaller area under the waveform curve, i.e., 1750 to 2150

μV/msec, and preferably from 1850 to 2050 μV/msec, indicate a DREZ having normal activity. Conversely, DREZ site activities with higher voltage and frequencies, i.e., above 10.0 μV, and preferably above 11.0 μV, and larger area under the waveform curve, i.e., above 2500 μV/msec, and preferably above 2750 μV/msec, indicate a DREZ having hyperactive activity. In some instance, the spontaneous electrophysiologic recording is repeated for reliability. Note also that these values provided above are not meant to be exact, but rather to provide a starting point for interpreting DREZ activity in a patient with a spinal cord injury, however, one of skill in the art could establish satisfactory parameters for determining aberrant and non-aberrant values for DREZ activity.

The second DREZ recording technique is evoked neuroelectrical hyperactivity, which measures the sensory threshold of a constant-current sinusoidal stimulus from two electrodes applied to the skin within the distribution of a dermatome. The electrical stimulus activates the nerve fibers directly because the current levels are below those needed to stimulate the actual receptors in the skin, and is performed directly before or after measuring electrical activity in the DREZ using the spontaneous neuroelectrical activity. Dotson, *J Clin. Neurophysiol,* 14:32–45 (1997). In preferred embodiments of the present invention, a frequency of approximately 5 Hz is used to selectively activate the unmyelinated C-fibers, including the polymodal and sympathetic C-fibers. Katims et al., *Appl Neurophysiol.,* 49:86–91 (1986); Schmidt et al., *J Neurophysiol.,* 78:2641–2648 (1997).

Testing is performed in accordance with the information provided by the somatotopic map, which can be caudal to, at, and cephalad to the level of injury in a patient with a SCI. In one embodiment of the present invention, a mean threshold for C-fiber perception above 0.30 mA, using a frequency of approximately 5 Hz, was considered abnormal. In a preferred embodiment of the present invention, a mean threshold for C-fiber perception above 0.35 mA, again using a frequency of approximately 5 Hz, was considered abnormal.

Note that TCS is also used pre-operatively to confirm the most cephalad potential aberrant DREZ sites in a patient with a SCI, where C-fiber perception is established by correlating skin dermatomal thresholds with normal and abnormal skin dermatomes reported by patients and corroborated by SCI therapist. As such, potential "hot" or abnormal DREZ are identified by the patient, confirming the extent of the most cephalad aberrant DREZ that the surgeon must eradicate.

Somatotopic Mapping and the Level of Pain

The invention provides a method for identifying an aberrant DREZ(s) in a patient with a SCI by mapping the level of injury and the regions of perceived pain in the patient against a somatotopic map prepared in accordance with the present invention. In particular, the identification of potential aberrant DREZ in a patient is based on correlating a patients perceived pain (and location of injury) with DREZ sites that have been identified in other patients having similar types of pain and locations of injury. For example, pain, i.e., foot, leg, chest, etc, in the patient can be correlated with pre-determined potential hyperactive DREZ site(s), i.e., T10, T11, T12, L1, etc., found through mapping in other patients.

The somatotopic map of the present invention corresponds to data from a series of patients and provides a 'standard curve,' where the location of any one patients' pain can be correlated to a standardized potential pain generating DREZ site. For example, a patient that has pain localized to his or her foot would likely show a hyperactive DREZ site at L1, as determined by reference to the completed somatotopic map (see Example II).

Patients for use in preparing the somatotopic map preferably had localized perceived pain that corresponded to localized and measured hyperactive DREZs. In this sense, five initial patients were used to prepare the illustrative map shown below in Table 6 (Example II). Patient 1 exhibited only foot pain, patients 2 and 3 exhibited only upper and lower leg pain, and patients 4 and 5 exhibited only gluteal, rectal and perirectal pain. A determination of DREZ hyperactivity was conducted in each patient: patient 1, having the isolated foot pain, demonstrated hyperactivity solely at the L1 DREZ; the two patients let pain, exclusive of foot, gluteal, rectal and perirectal pain, demonstrated hyperactivity solely at the T11 and T12 DREZs; the two patients with isolated gluteal, rectal and perirectal pain demonstrated hyperactivity solely at the T8, T9 and T10 DREZs.

The illustrative somatotopic map did not fit with traditional dermatomal mapping. However, the mapping data indicated a possible correlation with the sympathetic nervous system. Neuroanatomical dissection and clinical study have suggested that the sympathetic supply to 'end' organs of the lower extremities originates in caudal thoracic and cephalad lumbar spinal cord segments, to the head and neck, cephalad thoracic spinal cord segments, and to regions in between, by the intervening spinal cord segments. Pick, The Autonomic Nervous System: Morphological, Comparative, Clinical and Surgical Aspects, Philadelphia: J. B. Lippincott, 1970; Yokota et al., Brain 114:1381–1394 (1991). Afferent sympathetic supply may follow the efferent supply. Browder, *Am J Surg* 18:100–102 (1932); Echlin, *J Neurosurg* 530–533 (1949); Harris, *Brit Med J* 2:112–115 (1936); Pick, The Autonomic Nervous System: Morphological, Comparative, Clinical and Surgical Aspects, Philadelphia: J. B. Lippincott, 1970; Shields, *J Clin Neurophysiol* 10:2–13 (1993). Using data provided by the illustrative somatotopic map, it is believed that pain occurring distal from an injury site (below-level pain) is mediated significantly by the sympathetic nervous system. It is also believed that anatomic regions of perceived pain are somatotopically mapped to specific DREZ segments of the spinal cord. Specifically, lumbar segments (L1 in particular) mediate pain from the feet, T11 and T12 segments, the leg, and T8–T10 segments, the gluteal, rectal and perirectal regions. More cephalad segments would mediate pain the truncal region. It is also believed that cephalad segments could mediate pain subtended by those in more caudal segments by way of the sympathetic chain or interneuronal pathways.

Somatotopic maps prepared using the methods of the present invention, as well as the illustrative somatotopic map of the present invention, can be used alone or in combination with patient specific TCS and spontaneous neuroelectric activity to identify pain generating DREZ sites. In a preferred embodiment, data from TCS, spontaneous neuroelectric activity and somatotopic mapping are compared to identify a target pain generating or aberrant DREZ site(s) in a patient in anticipation to treating the identified aberrant DREZ site(s).

Methods of the present invention have been used to determine (and confirm) that at-level pain is likely mediated through traditional pain pathways (e.g., spinothalamic tracts) corresponding to the DREZ at the level of injury. Below-level pain has proven more interesting. Data of neuroelectic hyperactivity in the DREZs of all patients with below-level pain, whether spontaneous or evoked by TCS, have been correlated with specific regions of perceived pain. If pain occurred exclusively in the feet, with no perception of pain in more cephalad dermatomes, then hyperactivity was found only in the L1 DREZ with no involvement of more cephalad DREZs (one out of one case). If the most cephalad perception of pain occurred in dermatomes of the upper and lower leg, then hyperactivity was found in the T11 or T12 DREZs (10 out of 11 cases), with no involvement of more cephalad DREZs. If the most cephalad perception of pain occurred in dermatomes of the gluteal region, groin rectum, or genitalia, then hyperactivity was found in the DREZs of T8–T10 (15 out of 17 cases), with no involvement of more cephalad DREZs. If the most cephalad perception of pain occurred in truncal dermatomes, then hyperactivity was found in DREZs more cephalad than T8 (one out of one case) (see Table 7). Such strong correlation is consistent with the L1 DREZ mediating pain from the feet, the T 11 and T12 DREZs pain from the upper and lower leg, the T8–T10 DREZs, pain from the gluteal region, groin, rectum and genitalia, and DREZs more cephalad, pain from the trunk. The sympathetic nervous system provides, in part, an intriguing fit. Pain perceived more distal to regions mediated by a specific DREZ are likely due to communication through the sympathetic chain or interneuronal pathways.

Note also the present invention envisions the use of standard dermatomal maps for the identification of potentially aberrant DREZ in a patient with a spinal cord injury (standard dermatomal maps are well known in the art).

Identifying and Eradicating Pain Generating DREZ

FIG. 1 illustrates one method for reliably identifying and eradicating pain generating DREZ in accordance with the present invention. In step 100, the history of the patient having a spinal cord injury it obtained. The history typically includes a discussion with the patient of the type and location of their pain and of the steps the patient has taken to non-surgically alleviate the pain. In some instances, the patient may be required to exhaust non-surgical alternatives to relieving the pain before proceeding with the methods of the present invention. The history also typically includes an examination of the patient to confirm the location of the spinal cord injury, including a physical exam of the patient and a series of imaging techniques, e.g., cat scan, MRI, etc, on the spinal cord of the patient.

Utilizing the location of the injury, and the patient's perceived pain, obtained from the patients history, an initial determination of the potential aberrant DREZ is performed. In step 102, the patients perceived pain and level of injury are compared to the previously prepared somatotopic map (as described above and in the Examples below). The comparison of the patients individual parameters, perceived pain and level of injury, to the somatotopic map provides a template for identifying the potential aberrant DREZ(s) involved in the generation of pain in the patient.

If a patient has an injury to L1 or below, the comparison to the somatotopic map will provide an extremely reliable indication as to the range of potential DREZ that the surgeon must further investigate for "hot" activity. The range of potential aberrant DREZ are typically cephalad to the injury, as is expected. However, as the injury site moves above L1, the surgeon will use the somatotopic map to look for DREZ both cephalad and, surprisingly, caudal to the level of injury. Looking caudal to the injury site is a novel aspect of the present invention and is supported by the illustrative data in the Examples that follow.

Illustrative examples of step 102 include: if a patient presents with pain in the trunk, the mapping data shows that the potential aberrant DREZ will map between T1 and T6, for a patient with pain in the legs and feet, the mapping data shows that the aberrant DREZ will map between T11 and L1, and for a patient with pain in the buttock, rectum and/or genitals, the mapping data shows that the aberrant DREZ will map between T7 and T10.

As such, the somatotopic map provides the most cephalad potential "hot" DREZ activity in relation to the level of injury. Further, the somatotopic map provides potential aberrant DREZ sites caudal to the level of injury, where the patient complains of pain in dermatomes associated with DREZ sites below the site of injury.

It is believed that the cord below the injury in these instances may be functional and may have "hot" DREZ which can create pain, likely by routing the pain signal around the transected cord or, in cases where the cord in only partially transected, through the damaged cord.

In step 104, a TCS is optionally performed on the patient pre-operatively to confirm the "hot" DREZ between the level of injury in the patient and the most cephalad aberrant DREZ. The dermatomes corresponding to the DREZ at the site of injury, and above, are tested via TCS (as discussed above and the Examples below) to determine what current the patient perceives as being painful. At this point the DREZ are un-exposed, i.e., have not been surgically exposed. At the conclusion of step 104, the surgeon has a reliable indication of the potential "hot" DREZ that will need to be tested further using the spontaneous neuroelectrical activity and TCS techniques on the exposed DREZ.

In step 106, the surgeon exposes the spinal cord for DREZ microcoagulation, exposing the spinal cord between the levels of potential aberrant DREZ sites, as determined in steps 102 and 104. In step 108, each potential DREZ is evaluated for spontaneous electroencephalographic activity (see above and Examples below). A positive result both confirms and positively identifies a DREZ as an aberrant or pain generating DREZ. In step 110, TCS is performed on each of the same potential DREZ, as determined in steps 102 and 104, to provide an independent "evoked" response to identify aberrant or pain generating DREZ (especially important where a pain generating DREZ is not in a process of spontaneous electroencephalographic activity (in a calm or non-pain generating state). Note that steps 108 and 110 can be performed in either order. Also note that if a DREZ site is "hot" by one or the other direct recording techniques, the DREZ will be eradicated. However, if a result in either step 108 or 110 causes the surgeon concern that the electrical equipment is not operating properly, the surgeon will repeat the analysis or rely on the data from either the spontaneous electroencephalographic activity or TCS techniques.

In step 112, the surgeon performs DREZ microcoagulation on the "hot" DREZ, as determined in steps 102–110. In step 114/116, an optional TCS and/or spontaneous electroencephalographic recording technique is performed on the still exposed and now lesioned DREZ to determine the effectiveness of surgical procedure to eliminate the aberrant electrical activity. Note that step 112 through 116 may be repeated when the lesioned DREZ continue to have aberrant electrical activity. Finally, in step 118, the patient is followed to determine the effectiveness of the above discussed procedures.

Pain Effecter Identification in Target DREZ

The present invention further provides a method for identifying effecters responsible in-whole or in-part for the 'central pain' perceived in patients with a SCI. Identified effecters could be used to identify existing medications having potential at relieving pain in patients with SCI, or be used to develop novel compositions for use in relieving pain in patients with SCI.

Figure 2:
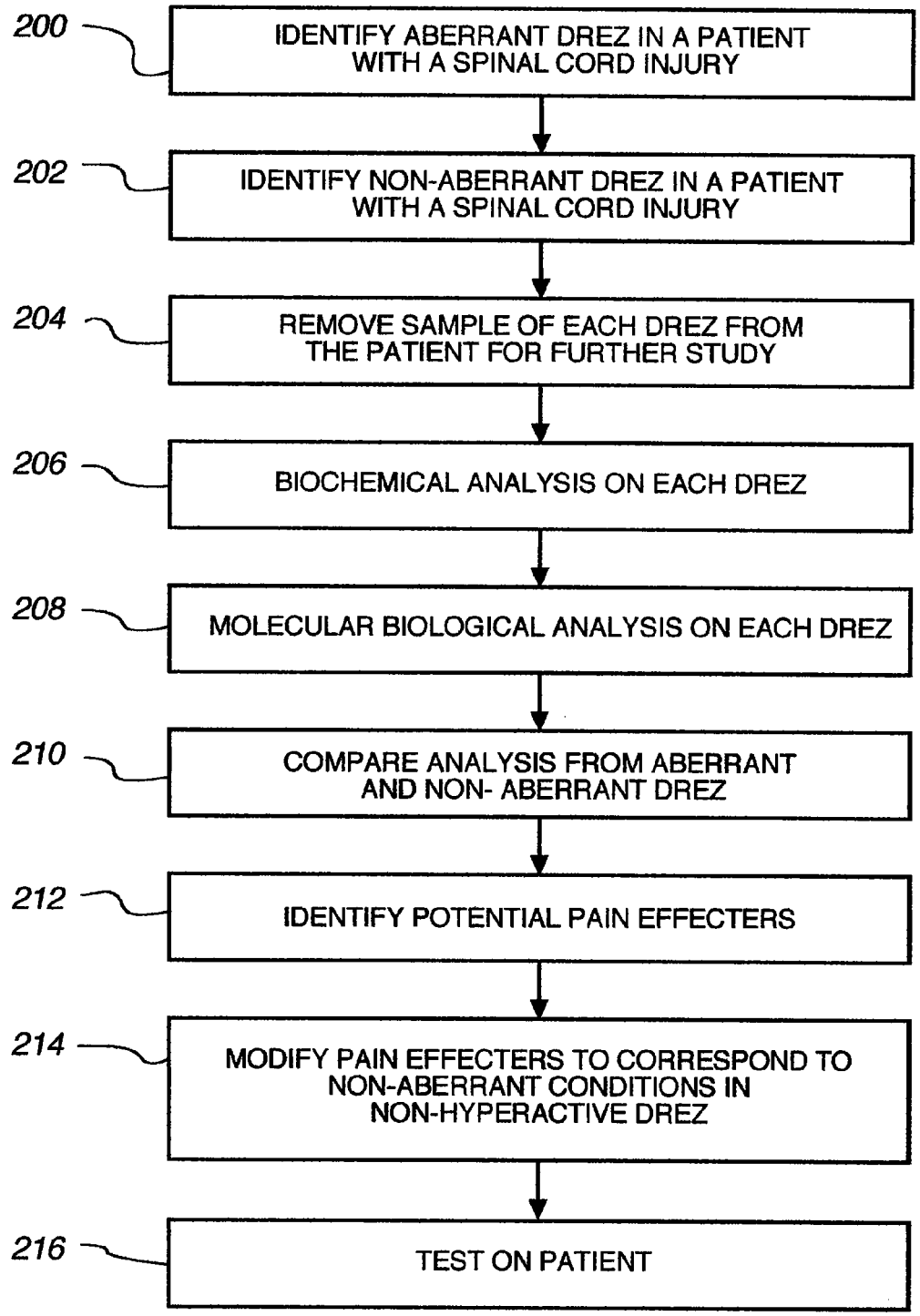
FIG. 2 is a flow diagram of a method for identifying pain effectors in aberrant DREZ(s) in accordance with the present invention.

FIG. 2 is a flow chart illustrating one embodiment of the steps required to identify an effecter of central pain in accordance with the present invention. In step 200, a hyperactive, pain generating DREZ site is identified in a patient with a SCI (note that hyperactive DREZ site identification is accomplished according to the methods discussed above and illustrated in the following Examples, all of which are in accordance with the present invention). In step 202, a non-hyperactive, and hence non-pain generating DREZ site, is identified in the same patient. In step 204, an appropriate sample of both the hyperactive, pain generating DREZ and non-hyperactive, non-pain generating DREZ is taken from the patient. Appropriate samples are typically taken by biopsy from the patient, typically of a 1 mm×1 mm×2 mm section of target DREZ. Note also that each sample is isolated and treated separately—to minimize any potential for cross-contamination between samples. In steps 206, 208, and 210 the samples removed from the patient are analyzed using one or more biochemical/molecular techniques to identify effecters present or at higher concentrations in the pain generating DREZ, than in the non-pain generating DREZ sample. These techniques, for example differential gene expression, protein separation by electrophoresis, etc., can be found in any of several well-known references, such as: *Molecular Cloning: A Laboratory Manual* (Sambrook et al. (1989)); *Gene Expression Technology* (Methods in Enzymology, Vol. 185, edited by Goeddel (1991) Academic Press, San Diego, Calif.); "*Guide to Protein Purification*" in *Methods in Enzymology* (Deutshcer, 3d., (1990) Academic Press, Inc.), *PCR Protocols: A Guide to Methods and Applications* (Innis et al. (1990) Academic Press, San Diego, Calif.); and *Gene Transfer and Expression Protocols*, pp 109–128, ed. Murray, The Humana Press Inc., Clifton, N.J.). Note also that the analysis may alternatively provide data that the pain-generating DREZ is devoid of a pain damping effecter or expresses a potential pain damping effecter at a lower concentration than in the non-pain generating DREZ. In any event, the methods will provide the identification of pain effecters in the present invention (step 212).

Note also that there are a number of potential target effecters that can be directly analyzed and compared in the pain generating and non-pain generating DREZ samples. For example, it is known that patients with SCI undergo a number of neurochemical changes—these include an accumulation of sodium channels, an increase in concentration or activity in excitatory amino acids (EAA), potential increases in EAA receptor levels, loss of spinal inhibitory mechanisms, e.g., γ-amino-butyric acid (GABA)ergic inhibition, hypofunction of opioid inhibitory system, e.g., increased levels of cholecystokinin, and hypofunction of the inhibitory monoaminergic system. Eide, *Spinal Cord* 36:601–612 (1998). Each of these potential targets could be directly analyzed in both the pain and non-pain generating DREZ sites, for example, the number of the EAA receptor, N-methyl-D-aspartic acid (NMDA), could be determined and compared between samples using a scatchard analysis and the results used to determine whether a NMDA antagonist would be a useful treatment for relieving pain in patients with SCI.

In step 214, potential target pain effecters or pain damping effecters are further studied to determine effective treatment regimes—typically animal studies are conducted as well as clinical studies in volunteer patients with SCI. Finally, in step 216, effecter antagonist and/or pain damping effecter replacements are tested on patients with SCI and hyperactivity of DREZ sites determined.

Having generally described the invention, the same will be more readily understood by reference to the following examples, which are provided by way of illustration and are not intended as limiting.

EXAMPLE

Example I

INTRAMEDULLARY ELECTRICAL GUIDANCE COMBINED WITH TRANSCUTANEOUS C-FIBER STIMULATION (TCS) OF DREZ LESIONING SUBSTANTIALLY IMPROVES PAIN OUTCOME IN PATIENTS WITH CENTRAL PAIN CAUSED BY TRAUMATIC SPINAL CORD INJURY.

Clinical Materials and Methods: Forty-one patients aged nineteen to seventy-two were selected for study within the parameters of the present invention, each having sustained traumatic thoracic or thoracolumbar spinal cord injuries (see Tables 1, 2 and 3). Thirty-eight of the patients were men and three patients were women, the median age for all patients was forty-six. Within the group, sixty-three percent of the patients experienced pain immediately after injury, eighty-four percent of patients experienced pain within two months of injury, ninety-five percent of patients experience pain within six months of injury, and one-hundred percent experienced pain within one year of the injury. The median duration of pain experienced prior to the methods of the present invention was approximately sixty-two months, with a range of five to four-hundred and forty-seven months (see Table 4). Note that the patients experienced pain in dermatomes at and immediately caudal to the level of injury in eight patients (at-level pain) and in regions more than two dermatomes caudal to the level of injury in thirty-one patients (below-level pain), and both at-level and below-level in two patients.

Nine of the patients in the group (Group 1) underwent DREZ microcoagulation for central pain using spontaneous neuroelectric hyperactivity in the DREZ as a guide. These patients were aged nineteen to fifty years old, with a median age of forty-four (all were male). Thirty-three percent of these patients experienced pain immediately after injury, eighty-nine percent of the patients experienced pain within two months of injury, and one-hundred percent experienced pain within three months of injury. Median duration of pain experienced prior to undergoing the methods of the present invention was sixty-two months with a range of five to two-hundred sixty-one months (see Table 4). Within this group, two patients had at-level pain, five had below-level pain and two had a combination of at-level and below-level pain.

Thirty-two patients in the group (Group 2) underwent DREZ microcoagulation for central pain using a combination of spontaneous neuroelectric hyperactivity and evoked hyperactivity during TCS of the DREZ as a guide. These patients were aged twenty to seventy-two years old, with a median age of forty-seven. Twenty-nine of these patients were make and three were female. Seventy-one percent of these patients experienced pain immediately after injury, eighty-two percent of patients experienced pain within two months of injury, ninety-four percent of patients experienced pain within six months of injury and one-hundred percent of patients experienced pain within one year of injury. Median duration of pain experienced by this group of patients was sixty-one months, with a range of five to four-hundred forty-seven months (see Table 4). Six of these patients experienced at level pain, twenty-five patients experienced below-level pain and one experienced at-level and below-level pain.

Pain in all forty-one patients could occur continuously, could wax and wane in intensity, could occur in bursts of severity, and could occur cyclically, e.g., every other day or even every other week. In general, pain was exacerbated with any noxious insult to the body such as skin sore or urinary tract infection. Altitude and weather changes could also influence the pain. Pain always occurred in regions of the body with absent or impaired sensation. If pain occurred at-level and below-level, the pains were different in character.

TABLE 1

Causes of Injury

| Type of Accident | All (n = 41) | Group 1 (n = 9) | Group 2 (n = 32) |
|---|---|---|---|
| Motor Vehicle Accid. | 19 | 6 | 13 |
| Fall | 10 | 1 | 9 |
| Gun Shot Wound | 5 | 1 | 4 |
| Traumatic Blow | 4 | 0 | 4 |
| Ped vs Auto | 1 | 1 | 0 |
| Airplane Crash | 1 | 0 | 1 |
| Bicycle Accident | 1 | 0 | 1 |

TABLE 2

Vertebral Level of Injury

| Vertebral Level of Injury | All (n = 41) | Group 1 (n = 9) | Group 2 (n = 32) |
|---|---|---|---|
| T4 | 1 | 0 | 1 |
| T6 | 1 | 0 | 1 |
| T6–7 | 1 | 0 | 1 |
| T7 | 2 | 0 | 2 |
| T9 | 1 | 1 | 0 |
| T10 | 2 | 1 | 1 |
| T10–11 | 1 | 0 | 1 |
| T11 | 9 | 1 | 8 |
| T11–12 | 2 | 1 | 1 |
| T12 | 8 | 1 | 7 |
| T12–L1 | 6 | 2 | 4 |
| L1 | 7 | 2 | 5 |

TABLE 3

American Spinal Injury Association

| Category | All (n = 41) | Group 1 (n = 9) | Group 2 (n = 32) |
|---|---|---|---|
| ASIA A | 36 | 8 | 28 |
| ASIA B | 0 | 0 | 0 |
| ASIA C | 3 | 1 | 2 |
| ASIA D | 2 | 0 | 2 |

TABLE 4

Pain Descriptors

| Character of Pain | All (n = 41) | Group 1 (n = 9) | Group 2 (n = 32) |
|---|---|---|---|
| Burning | 91% | 89% | 62% |
| Sharp/Stabbing | 61% | 56% | 62% |
| Cramping/Pressure | 38% | 22% | 38% |
| Stinging/Pins & Needles | 23% | 22% | 24% |
| Electrical/Shooting | 12% | 22% | 9% |

TABLE 4-continued

Pain Descriptors

| Character of Pain | All (n = 41) | Group 1 (n = 9) | Group 2 (n = 32) |
|---|---|---|---|
| Aching | 12% | 0 | 5% |
| Hypersensitivity to Touch | 7% |  | 9% |
| Cold/Freezing | 2% |  | 3% |
| Vibrating | 2% |  | 3% |

Preoperative Procedures: All patients to undergo the methods of the present invention underwent preoperative evaluation with plain x-ray and magnetic resonance imaging (MRI), or cat scan (CT) myelography to evaluate the spine and spinal cord. Patients with suicidal ideation underwent psychological evaluation and preoperative clearance. Prior to surgical treatment in occurrence with the present invention, all patients underwent extensive pharmacologic treatment including administration of oral tricyclic antidepressants (TCA), antiseizure medications, Baclofen, Klonopin, and narcotic analgesics. Several of the patients also had a pump placed for intrathecal infusion of narcotics, Baclofen, Clonidine or local anesthetic. Note that several of the patients had a spinal cord stimulator placed. In general, the oral medications administered to the patients were ineffective, however, some of the TCAs (Neurontin and Klonopin) took the "edge off" of the pain. Intrathecal infusion of the medications described and spinal cord stimulators were ineffective at relieving pain in the forty-one above described patients.

DREZ Recording Techniques:

Spontaneous Neuroelectric Activity: Multilevel laminectomies were performed on each (forty-one) patient as is known to one of skill in the art. Briefly, laminectomies were performed to expose the spinal cord at, cephalad, and one segment caudal to the level of injury. Spinal levels were determined by intraoperative x-ray. Intraoperative ultrasonography was used to identify the injury site. The dura was opened and the DREZs identified. Electrophysiologic analysis of the DREZs were then performed on level caudal to the injury site, and depending on the recorded electrophysiologic data, up to 5 DREZ levels cephalad. To perform such an analysis, an active electrode was inserted into the specific target DREZ. The active electrode used was a 25 mm TECA MF 25 monopolar electrode with the distal 2 mm exposed. The electrode was implanted "free hand" in the DREZ with use of the intraoperative microscope to a 2 mm depth. The axis of implantation was approximately 35°–45° medially and was the same axis used fro DREZ microcoagulation. Ground and reference Glass subdermal (EEG) electrodes were placed in exposed paraspinous muscle bilaterally. Spontaneous electrophysiologic recordings were made with a Cadwell Spectrum 32 evoked potential averager at a gain setting of 50 with the high frequency filter set at 3 KHz and the low frequency filter at 100 Hz. The recordings were one second in duration.

Evoked Neuroelectric Hyperactivity: Thirty-two of the forty-one patients additionally underwent DREZ recordings during transcutaneous C-fiber stimulation (TCS) using the Neurometer® current perception threshold (CPT) device. The CPT device measures the sensory threshold of a constant current sinusoidal stimulus from two electrodes applied to the skin within the distribution of a dermatome. The electrical stimulus activates the nerve fibers directly because the current levels are below those needed to stimulate the actual receptors in the skin. Dotson, *J Clin Neurophysiol* 14:32–45, 1997. Stimulation at a frequency of 5 Hz selectively activates the unmyelinated C-fibers (Katims et al., *Appl Neurophysiol* 49:86–91, (1986), including the polymodal and sympathetic C-fibers. Schmidt et al, *J Neurophysiol* 78(5):2641–2648, (1997).

Preoperative testing of dermatomal skin sensation in a C-fiber frequency band was performed caudal, at, and cephalad to the level of injury, in the thirty-two patients using the Neurometer® CPT device. Eide, *Spinal Cord,* 36:601–612, (1998). A criterion for C-fiber abnormality was established by correlating skin dermatomal thresholds with normal and abnormal skin dermatomes reported by the patient and corroborated by experienced SCI therapists. The patient group was employed to set the criteria, rather than normal volunteers, because: 1) most of the patients were on pain medication, 2) patients were frequently in pain during the assessment, and 3) chronic pain patients have often developed higher tolerances for pain.

Parameters of Evoked Neuroelectric Hyperactivity: The mean threshold for C-fiber perception in this patient group was 0.177 mA of 5 Hz current in skin dermatomes perceived as normal. The median was 0.183 mA with a standard deviation of 0.073 mA. The upper ninety-five percent confidence interval was 0.196 mA. The criterion for abnormality of C-fiber perception was arbitrarily set at 0.35 mA, approximately two standard deviations above the upper ninety-five percent confidence interval. The assumption was made that a 5 Hz-CPT threshold above 0.35 mA was a significant finding (see Table 5 for a specific instance of evoked hyperactivity in an illustrative patient, from T6 to T11). In general, the elevated thresholds were found in dermatomes at and cephalad to the neurologic level of injury, in patients who were sensory complete, but occasionally were found in dermatomes immediately caudal to the sensory complete neurologic level. These same skin dermatomes, with elevated and presumed abnormal thresholds, were stimulated above threshold operatively. Intramedullary recordings, as previously described, were then made in the DREZs corresponding to the particular skin dermatome.

TABLE 5

Preoperative CPT Dermatomal Mapping

| Site | Left Side C Fiber 5 Hz |
|---|---|
| T6 | 0.29 mAmp |
| T7 | 0.36*mAmp |
| T8 | 0.90*mAmp |
| T9 | no response |
| T10 | no response |
| T11 | no response |

*Note elevated thresholds in the zone of partial sensory preservation

Data Analysis:

Spontaneous Neuroelectric Recordings: The initial data of all forty-one patients were analyzed by root mean square (RMS) as expressed in micro volts, frequency and voltage in the waveform by fast Fourier transform (FFT) and area under the waveform curve (expressed in μV per millisecond). These same analysis were performed on data subsequent to DREZ microcoagulation. Both RMS analysis and area under the waveform curve provided a single numerical value of the recorded neuroelectric energy. Analyses were performed by a subroutine in the Cadwell Spectrum 32 software. A phenomenon that we describe as "spindles" was examined by passing the initial data through a tight digital filter with a band pass of 65–100 Hz. A visual count was made of the number of spindle bursts in the one second recording, excluding artifacts caused by cardiac electrical activity or electrode movement. Using the analysis described, two distinct electrophysiologic DREZ activities were found.

Figure 3A:
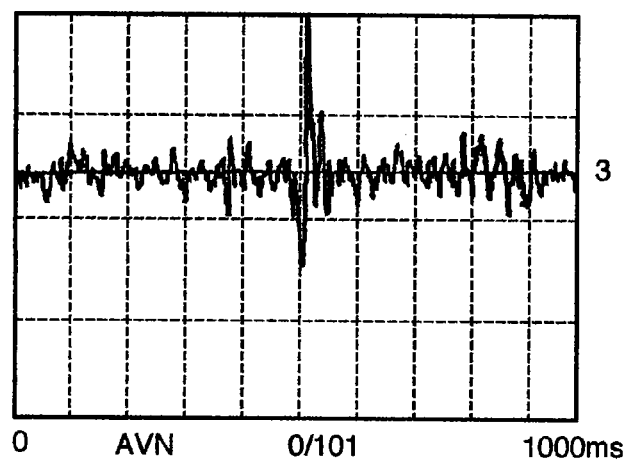
FIGS. 3A–F illustrates operative electrophysiologic analysis on a patient prior to DREZ microcoagulation. Initial recording from the (L) T6 DREZ showing normal neuroelectric activity (RMS is 6.76 μV/Area of 2372 μVms) (3A); Fast Fourier Transform (FFT) of (L) T6 initial recording, note the low electric activity throughout the frequency spectrum (frequencies from 5–25 Hz are reflections of EKG activity) (3B); Band pass filters, 65–100 Hz, of (L) T6 initial recording, spindles do not exceed two per second (3C); Initial recording from the (L) T7 DREZ showing abnormal neuroelectric activity (note the ten-fold increase in peak-to-peak voltage with change in frequency components compared to above)(RMS is 15.57 μV and the Area is 6158 μVms) (3D); FFT of initial recording of (L) T7 DREZ, note presence of high electrical activity across frequency spectrum (3E); And band pass filter, 65–100 Hz, of initial recording (L) T7 DREZ, spindles exceed three per second (3F). It should be noted that the data shown in Table 5 is from the same patient as shown in this Figure.
Figure 3B:
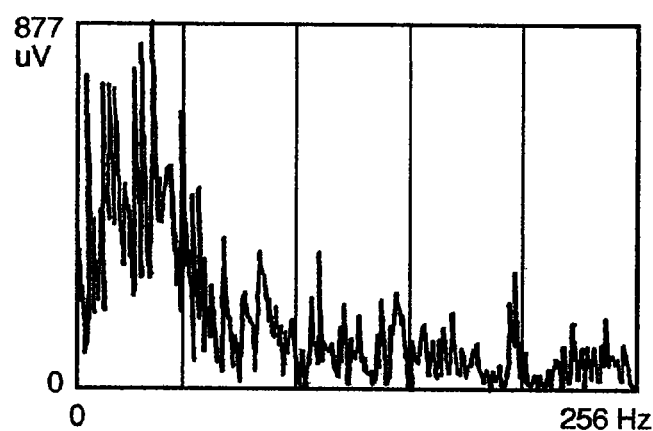
Figure 3C:
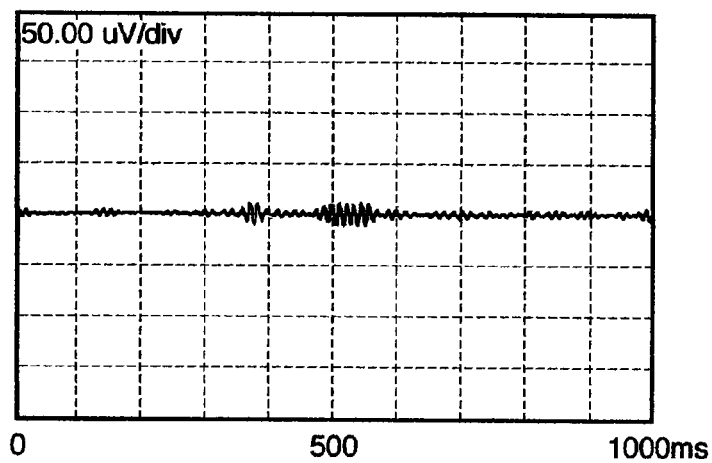
Figure 3D:
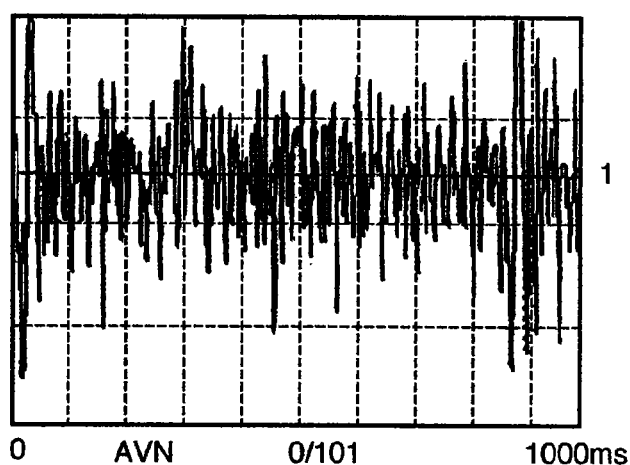
Figure 3E:
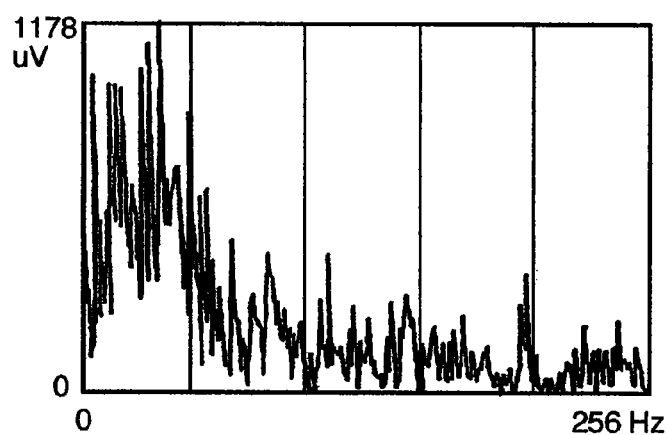
Figure 3F:
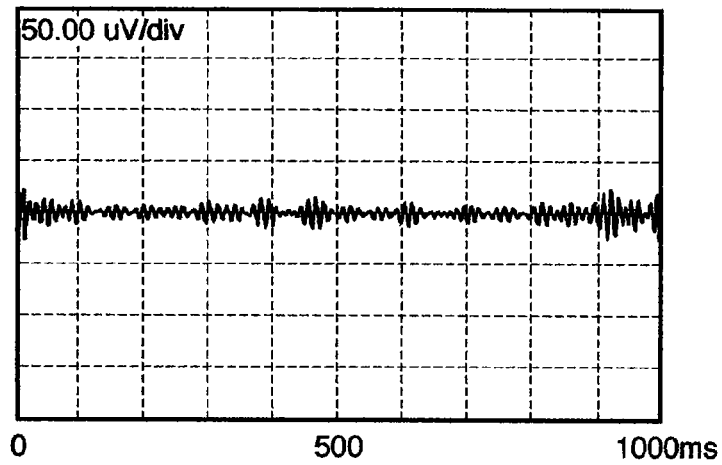
Figure 4A:
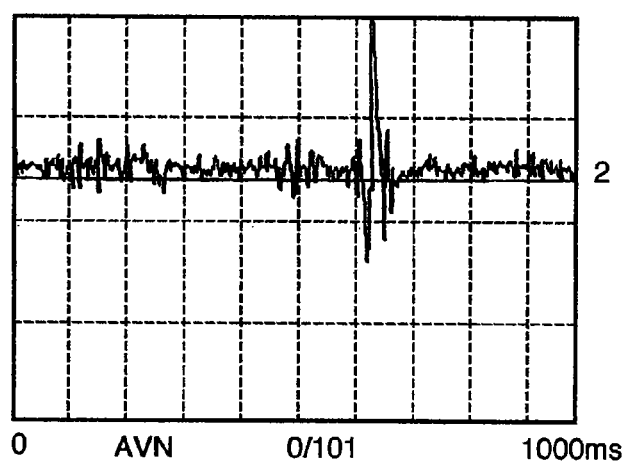
FIGS. 4A–C illustrates an operative electrophysiologic analysis subsequent to DREZ microcoagulation on the patient illustrated by FIG. 3. Initial recording of (L) T7 DREZ (RMS is 4.24 μV and Area is 1161 μVms) (4A); FFT of initial recording of (L) T7 DREZ, note the return skewing of the frequency plot toward lower frequencies and the greatest voltage at 30 Hz (4B); And band pass filters, 65–100 Hz of initial recording of (L) T7 DREZ, spindles do not exceed two per second (4C).
Figure 4B:
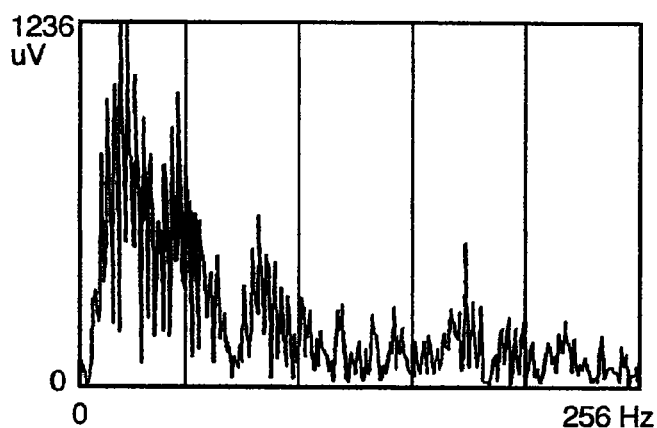
Figure 4C:
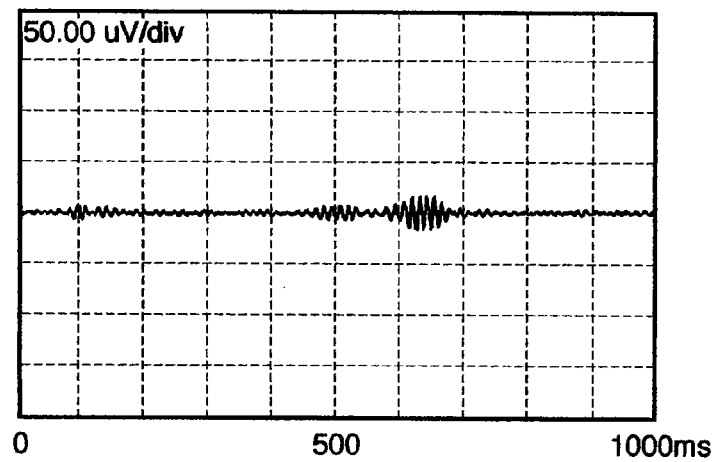

Those activities showing lower voltage and frequencies, smaller area under the waveform curve, and fewer than three spindles were considered normal DREZ activity. FIGS. 3A–C shows normal DREZ activity corresponding to the data in Table 5, (L) T6 DREZ. Those showing higher voltage and frequencies, greater area under the waveform curve, and greater than three spindles, were regions of abnormal neuroelectric hyperactivity. For example, FIGS. 3D, E, and F provide data corresponding to Table 5, (L) T7 (Note that the data shown in FIG. 3 corresponds to the T6 and T7 TCS data from the same patient shown in Table 5). Analyses were also performed subsequent to DREZ microcoagulation of regions of abnormal neuroelectric hyperactivity. One should note diminished values of activity, even less than those consistent with normal DREZ activity, (FIGS. 4A, B, and C, showing data from the same patient as illustrated in FIG. 3, after DREZ microcoagulation).

Figure 5A:
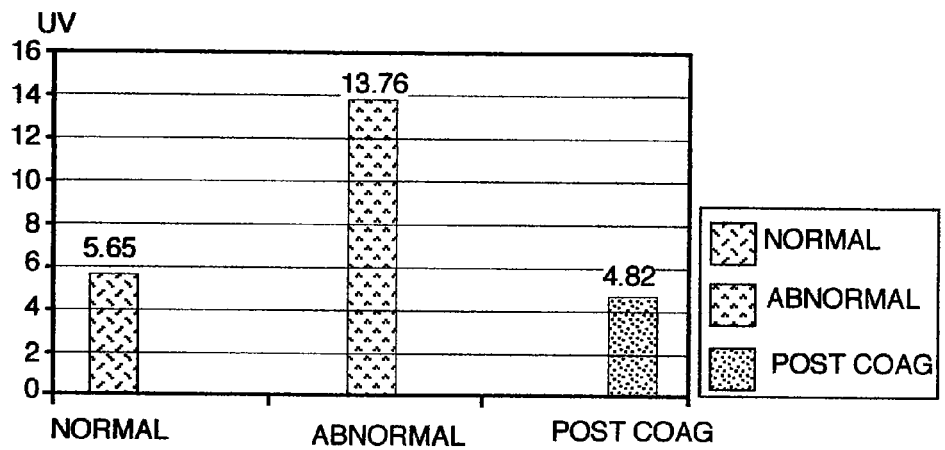
FIGS. 5A–C is a plot of mean RMS voltage, normal versus abnormal versus post-DREZ microcoagulation (5A); a plot of the mean area under the waveform curve, normal versus abnormal versus post-DREZ microcoagulation (5B); And a plot of the average spindles, normal versus abnormal versus post-DREZ microcoagulation (5C).
Figure 5B:
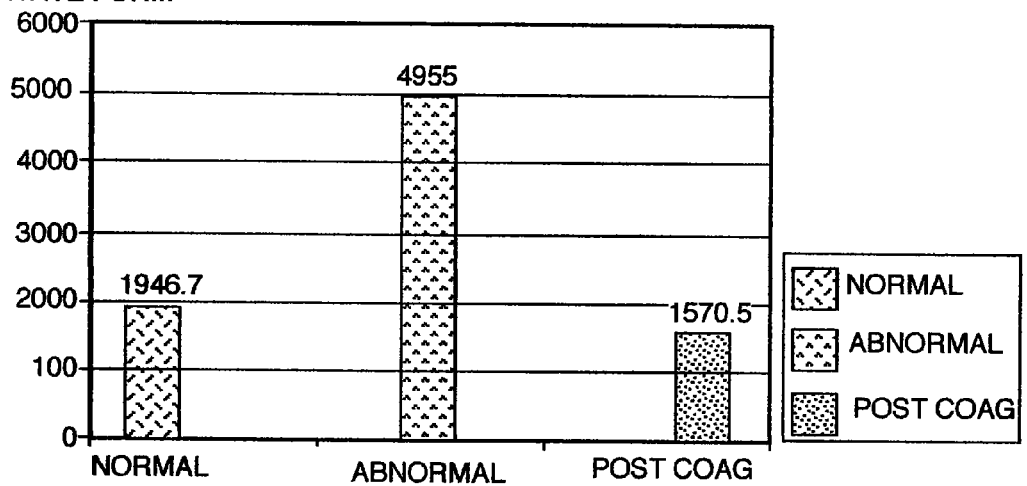
Figure 5C:
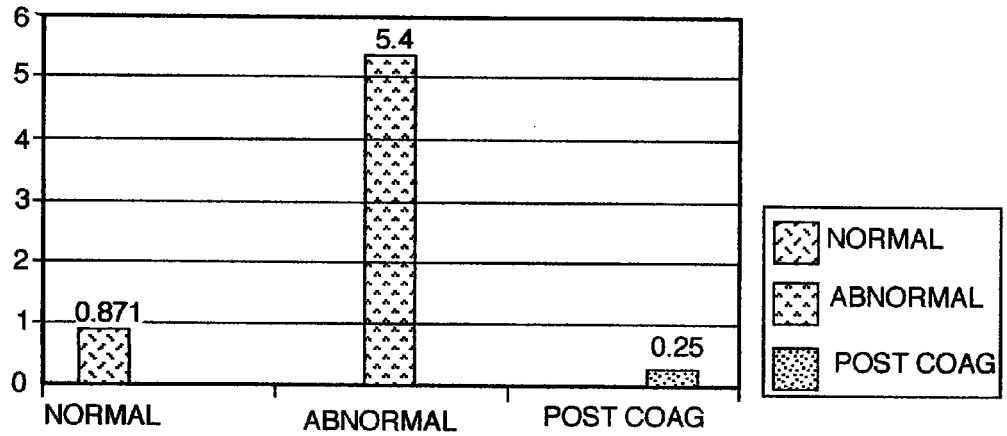

The mean RMS value for normal sites was 5.65 μV (standard deviation of 2.2 μV), for hyperactive sites 13.76 μV (standard deviation of 6.76 μV), and post-coagulation sites 4.28 μV (standard deviation of 1.68 μV) (see FIG. 5A). A one-way ANOVA on the RMS values was significant with $p<0.001$. Mean RMS values for the three sites were significantly different from each other with $p<0.005$ by Scheffe test. The mean area under the waveform curve value for normal sites was 1946.7 μVms (standard deviation of 706.34 μVms), for hyperactive sites 4995 μVms (standard deviation of 2410.6 μVms), and for post-coagulation sites 1570.5 μVms (standard deviation of 522.47 μVms) (see FIG. 5B). A one-way ANOVA on the area values was significant with $p<0.001$. Mean area values for the three sites were significantly different from each other with $p<0.001$ by Scheffe test. The mean number of spindles for the normal sites was 0.871 (standard deviation of 1.039), for hyperactive sites 5.4 (standard deviation of 1.30), and for the post-coagulation sites 0.25 (standard deviation of 0.585) (see FIG. 5C). The one-way ANOVA on the mean spindle was significant ($p<0.001$). Spindle values of post-coagulation sites were significantly diminished from the normal sites ($p<0.001$ by Scheffe test). The electrical measures were all strongly related to each other. Pearson correlations for RMS with area was 0.968, RMS with spindles was 0.7 and spindles with area was 0.799 were significant with $p<0.001$.

Figure 6:
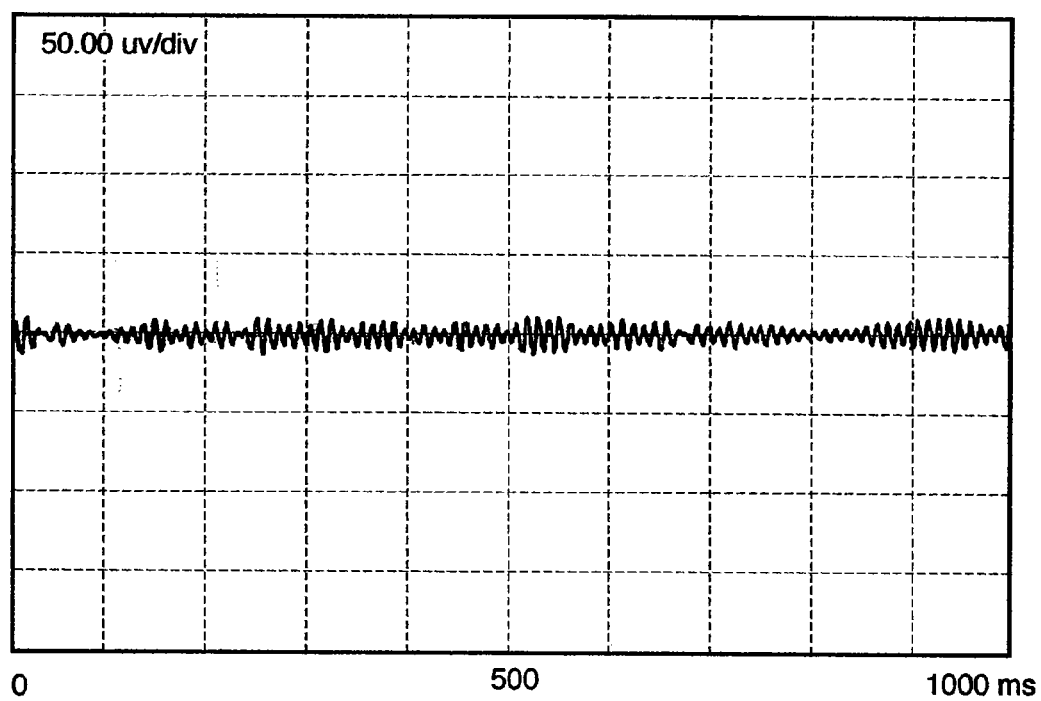
FIG. 6 illustrates a spindle analysis from (L) T6 DREZ in the patient illustrated in FIGS. 3 and 4, after TCS above threshold, note spindling greater than two per second.

TCS Recordings: TCS above threshold, of a skin dermatome judged as normal or abnormal, could be detected in a DREZ judged neuroelectrically as normal or abnormal, respectively, as an enhancement of neuroelectric activity. That is, an increase in RMS values, area under the waveform curve, and spindling could be found and is shown in FIG. 6. Greater intensity of stimulation would lead to a progressive elevation of the values described. In approximately eighty-nine percent of patients, operative stimulus of the normal skin dermatome by CPT analysis, immediately cephalad to regions of partial sensory preservation, was detected in the normal DREZ of the patient which was immediately cephalad to those demonstrating spontaneous neuroelectric hyperactivity. In seventy-two percent of patients, the most cephalad abnormal skin dermatome, as determined by preoperative CPT, was mapped and correlated with the most cephalad DREZ demonstrating spontaneous neuroelectric hyperactivity. These associations were statistically significant by chi square ($p<0.001$).

DREZ Lesioning Procedure: Seven of the nine Group 1 patients exhibited regions of spontaneous DREZ neuroelectric hyperactivity. In those seven patients, radio-frequency microcoagulation at 90° C. for approximately 30 seconds was performed to produce microthermal lesions with one millimeter of separation in all DREZs demonstrating spontaneous neuroelectric hyperactivity. Following the microcoagulation procedure, neuroelectric activity was again measured. If recorded traces showed absence of neuroelectric hyperactivity, no further lesions were made. If, however, recorded traces continued to show spontaneous neuroelectric hyperactivity, microlesioning was repeated. In the two cases where no spontaneous neuroelectric hyperactivity was found, an empiric technique (Freeman et al., *Arch Surg* 55:433–440, (1947)) was used wherein DREZ microcoagulation was performed at two DREZs cephalad to the level of injury and one below, with microcoagulation performed at 90° C. for 30 seconds.

In the thirty-two patients of Group 2, DREZ microcoagulation was guided by localization of spontaneous DREZ neuroelectric hyperactivity, as well as evoked DREZ hyperactivity during TCS of skin dermatomes with elevated C-fiber sensory thresholds. Microcoagulation was performed at 90° C. for 30 seconds with lesions 1 mm apart in all identified pain generators. Intramedullary recordings were repeated to ensure absence of spontaneous neuroelectric hyperactivity in these DREZ regions as well as evoked hyperactivity during TCS. In nine of the thirty-two patients, no spontaneous DREZ hyperactivity was found operatively. All patients had below-level pain. In these nine patients, operative TCS of skin dermatomes with elevated C-fiber sensory thresholds resulted in evoked neuroelectric hyperactivity in specific DREZs. These DREZs were the presumed pain generators. This guided radio-frequency microcoagulation of the DREZs in these nine patients where no spontaneous neuroelectric hyperactivity was found.

Results: DREZ microcoagulation of the first nine patients (Group 1), guided solely by spontaneous neuroelectric hyperactivity of the DREZ, resulted in fifty-six percent (five patients) achieving one-hundred percent pain relief, and seventy-eight percent (seven patients) achieving fifty to one-hundred percent pain relief. Both of these categories of pain relief were described as significantly improving the quality of life of the patient. Pain relief reported at less than fifty percent did not significantly improve the quality of the patient's life (two of nine patients). Follow-up on pain relief was from six to seven years to ensure that whatever degree of relief a patient felt was considered permanent.

In thirty-two patients (Group 2) undergoing DREZ microcoagulation with the addition of TCS guidance, eighty-four percent achieved one-hundred percent pain relief, and eighty-eight percent achieved fifty to one-hundred percent pain relief. Follow-up for this group was from one to six years. Twenty-six of the thirty-two patients had below-level pain. Eighty-one percent of the patients achieved one-hundred percent pain relief and eighty-five percent of the patients of this group achieved fifty to one-hundred percent pain relief. Six of the thirty-two patients had at-level pain and all achieved one-hundred percent pain relief.

Spontaneous neuroelectric hyperactivity was not found operatively in nine patients of this group (Group 2). TCS was the sole guide to DREZ microcoagulation in these patients. Eight of the nine patients achieved one-hundred percent pain relief. One of the nine patients failed to achieve pain relief and all nine patients had below-level pain.

Morbidity: Of the forty-one patients that make up the study described in this Example, thirty-three had complete pre- and postoperative ASIA sensory testing and thirty-five patients had complete pre- and postoperative ASIA motor testing. Ditunno et al., *Paraplegia*, 32:70–80, (1994). Pin-prick sensation was partially or completely lost in the corresponding DREZs of microcoagulation in twenty-seven of the thirty-three patients (82%). Light touch sensation was partially or completely lost in the corresponding DREZs of microcoagulation in twenty-two of the thirty-three patients (69%). Note that five of the thirty-five patients (14%) experienced motor deficit and that other complications, including, cerebrospinal fluid leak (9.3%), wound infection (2.3%), delayed spinal instability (7.6%), pulmonary embolus (2.3%) and wound dihisscence (2.3%) occurred. There were no deaths in either of the study groups (1 or 2). Finally, note that 2.3% of patients developed a temporary pain at the new postoperative level of sensation, which resolved (approximately 4.7% developed a permanent, but minor, pain at their new level of sensation, graded 1–3 on a scale of 10).

Discussion: Spontaneous neuroelectric hyperactivity was found in the DREZs of the majority of tested spinal cord injured patients (30 of 41, 73%) and guided and facilitated DREZ lesioning. That spontaneous neuroelectric hyperactivity was absent operatively in twenty-seven percent of tested cases which was not unexpected because the patients did not always experience pain continuously, and the severity of the pain often waxed and waned, i.e., the hyperactivity of the DREZ are also expected to wax and wane (illustrating why using the evoked TCS technique is useful in identifying all the neuroelectric hyperactive DREZ).

In fifteen percent of the patients in the present study, repeat DREZ lesioning was required due to inadequacy of the initial microthermal lesions. Additionally, in sixty-two percent of patients with below-level pain, spontaneous DREZ hyperactivity was found three-to-five levels cephalad to the level of injury. This result is important, as the commonly reported empiric DREZ microcoagulation techniques call for treatment only two DREZ levels cephalad to the site of injury and lack a way to determine the adequacy of the lesioning (note that historically, empiric techniques have been found effective in only approximately twenty percent of patients with below-level pain. Friedman et al., J Neurosurg, 65:465–469, (1986); Ishijima et al., *Appl Neurophysiol*, 51:2–5, 175–187, (1988); Rath et al., *Acta Neurochir*, 138: 4, 364–369, (1996); Rath et al., Sterotact Funct Neurosurg, 68:1–4, 161–167, (1997).

A correlation between skin dermatomes demonstrating partial sensory preservation in a C-fiber frequency band (i.e., C-fiber central deafferentation) with DREZs demonstrating spontaneous neuroelectric hyperactivity allowed operative guidance of DREZ lesioning in the nine cases of the second study group where no spontaneous hyperactivity allowed operative guidance of DREZ lesioning in the nine cases of the second study group where no spontaneous hyperactivity was found at the time of surgery. These skin dermatomes of partial sensory preservation were stimulated operatively, and the corresponding DREZs identified by detection of evoked hyperactivity. Eight of these nine patients achieved one-hundred percent pain relief after DREZ microcoagulation was directed in this manner. All nine patients experienced below-level pain. This technique of TCS was useful as well for cases where spontaneous hyperactivity was measured. In these cases, the data provided information to facilitate the search for DREZ hyperactivity and provided a second localizing test, decreasing the possibility of failing to identify all pain generators. Subsequent improvement in pain outcomes was attributed to the addition of the TCS technique.

It is important to note that eighty-one percent of patients in the Group 2 experienced below-level pain. Of these patients, eighty-five percent achieved fifty to one-hundred percent pain relief and eighty-one percent achieved one-hundred percent pain relief. The data illustrated in this Example substantially exceeds pain relief outcome for below-level pain reported in the literature (Friedman et al., J Neurosurg, 65:465–469, (1986); Ishijima et al., Appl Neurophysiol, 51:2–5, 175–187, (1988); Rath et al., Acta Neurochir, 138: 4, 364–369, (1996); Rath et al., Sterotact Funct Neurosurg, 68:1–4, 161–167, (1997)). All six patients with at-level pain in Group 2 achieved one-hundred percent pain relief, exceeding outcomes reported in the literature. Id.

A decrease in loss of light touch sensation was achieved at lower temperatures of microcoagulation, i.e., at 75° C., in earlier experience. However, incomplete lesioning, persistence of hyperactivity, and in some cases, development of "squeezing pressure" pain at the new level of sensation, led to increasing the temperature of microcoagulation to 90° C. This higher temperature markedly reduced the need for repeat lesioning as well as the development of a new "squeezing pressure" pain. It is likely that the higher temperature destroys mechano- and pressure representation at deeper REXED layers, which may be left active and upregulated after lesioning at lower temperatures.

The data in this Example illustrate that the methods of the present invention, for patients with pain resultant from spinal cord injury, substantially improves pain outcomes compared to empiric techniques used to perform DREZ lesioning. This Example illustrates the usefulness of the present invention.

Example II

SOMATOTOPIC MAPPING OF DREZ ELECTRICAL DATA PROVIDES A USEFUL TOOL IN LOCALIZING PAIN GENERATING DREZS

Somatotopic Mapping: As shown in Example I, DREZ targeting with spontaneous neuroelectric hyperactivity and elevated dermatomal C-fiber thresholds correlate for a method to localize abnormal DREZ for microcoagulation. This data suggested that somatotopic mapping of specific DREZs to perceived regions of pain could result in the production of a somatotopic map having specific DREZ to perceived regions of pain.

Five patients provided data in the preparation of the map. One patient had only foot pain; two patients had only upper and/or lower leg pain; and two patients had only gluteal region/rectal/perirectal pain. The patient with isolated foot pain demonstrated hyperactivity solely at the L1 DREZ. The two patients with isolated leg pain, exclusive of foot, gluteal, rectal and perirectal pain, demonstrated hyperactivity solely at the T11 and T12 DREZs. The two patients with isolated with isolated gluteal, rectal and perirectal pain demonstrated hyperactivity solely at the T8, T9, and T10 DREZ (see Table 6). This data does not fit with traditional dermatomal mapping.

TABLE 6

Somatotopic Mapping

| Pain Location | T8 | T9 | T10 | T11 | T12 | L1 |
|---|---|---|---|---|---|---|
| Foot Only |  |  |  |  |  | X |
| Leg Only |  |  |  | XX | XX |  |
| Buttock Only | X | XX | XX |  |  |  |

Discussion: The above data suggest a correlation to the sympathetic nervous system. Neuroanatomical dissection and clinical study have suggested that the sympathetic supply to end organs of the lower extremities originates in caudal thoracic spinal cord segments, and to regions in between, by the intervening spinal cord segments. Pick: Autonomic Nervous System: Morphological, Comparative, Clinical and Surgical Aspects, Philadelphia: J. B. Lippincott, (1970); Yokota et al., Brain, 114:1381–1394, (1991). Afferent sympathetic supply has not been as well delineated, but may in part follow the efferent supply. Browder, Am J Surg, 18:100–102, (1932); Echlin, J Neurosurg, 530–533, (1949); Harris, Brit Med J, 2:112–115, (1936); Pick: Autonomic Nervous System: Morphological, Comparative, Clinical and Surgical Aspects, Philadelphia: J. B. Lippincott, (1970); Shields, J Clin Neurophysiol, 10:2–13, (1993). Bolstered from the data in this Example, several conclusions can be made: that pain occurring distal from the injury site (below-level pain) was mediated significantly by the sympathetic nervous system; that anatomic regions of perceived pain can be somatotopically mapped to specific DREZ segments of the spinal cord, i.e., lumbar segments (L1 in particular) are hypothesized to mediate pain from the feet, T11 and T12 segments, the leg, and T8–T10 segments, the gluteal, rectal, and perirectal regions. More cephalad segments would mediate pain in the truncal region. Additionally, it is hypothesized that cephalad segments could mediate pain subtended to those in more caudal segments by way of the sympathetic chain of interneuronal pathways. At-level pain was assumed to be mediated through more traditional pain pathways, e.g., spinothalamic tracts, corresponding to the DREZ at the level of injury.

Below-Level Pain: Data of neuroelectric hyperactivity in the DREZs of all patients with below-level pain, whether spontaneous or evoked by TCS, were correlated with specific regions of perceived pain. If pain occurred exclusively in the feet, with no perception of pain in more cephalad dermatomes, then hyperactivity was found only in the L1 DREZ with no involvement of more cephalad DREZs (in one of one case). If the most cephalad perception of pain occurred in dermatomes of the upper and lower leg, then hyperactivity was found in the T11 or T12 DREZs in ten out of eleven cases, with no involvement of more cephalad DREZs. In the most cephalad perception of pain occurred in dermatomes of the gluteal region, groin, rectum, or genitalia, then hyperactivity was found in the DREZs of T8–T10 in fifteen out of seventeen cases with no involvement of more cephalad DREZs. If the most cephalad perception of pain occurred in truncal dermatomes, then hyperactivity was found in DREZs more cephalad than T8 in one out of one case (see Table 7). Such strong correlation was consistent with the L1 DREZ mediating pain from the feet, the T11 and T12 DREZs pain from the upper and lower leg, the T8–T10 DREZs, pain from the gluteal region, groin, rectum and genitalia, and DREZs more cephalad, pain from the trunk.

The sympathetic nervous system provides, in part, an intriguing fit. Pain perceived more distal to regions mediated by a specific DREZ could be explained by communication through the sympathetic chain or interneuronal pathways.

TABLE 7

Somatotopic Mapping

| Location | L1 | T11 and/or T12 | T8–T10 | Above T8 |
|---|---|---|---|---|
| Foot | 1/1 | 8/11 | 13/17 | 1/1 |
| Upper and Lower Leg | | 10/11 | 15/17 | 1/1 |
| Lower Leg Buttock, Groin, Rectum, Genitalia | | 1/11 | 15/15 | 1/1 |
| Trunk | | | | 1/1 |

Example III

ILLUSTRATIVE PATIENTS HAVING NEUROELECTRICALLY ACTIVE DREZ BELOW THE LEVEL OF INJURY.

The following Example illustrates the finding that perceived pain in a patient with a spinal cord injury can be related to hyperactive DREZ sites below the level of injury to the spinal cord. A quadriplegic patient having chronic pain in both legs, feet, perirectal and gluteal regions presented for DREZ microcoagulation. After a complete history was performed on the patient, the methods of the present invention, as essentially described in Examples I and II, were performed so as to identify and eradicate the pain generating DREZ.

Figure 7A:
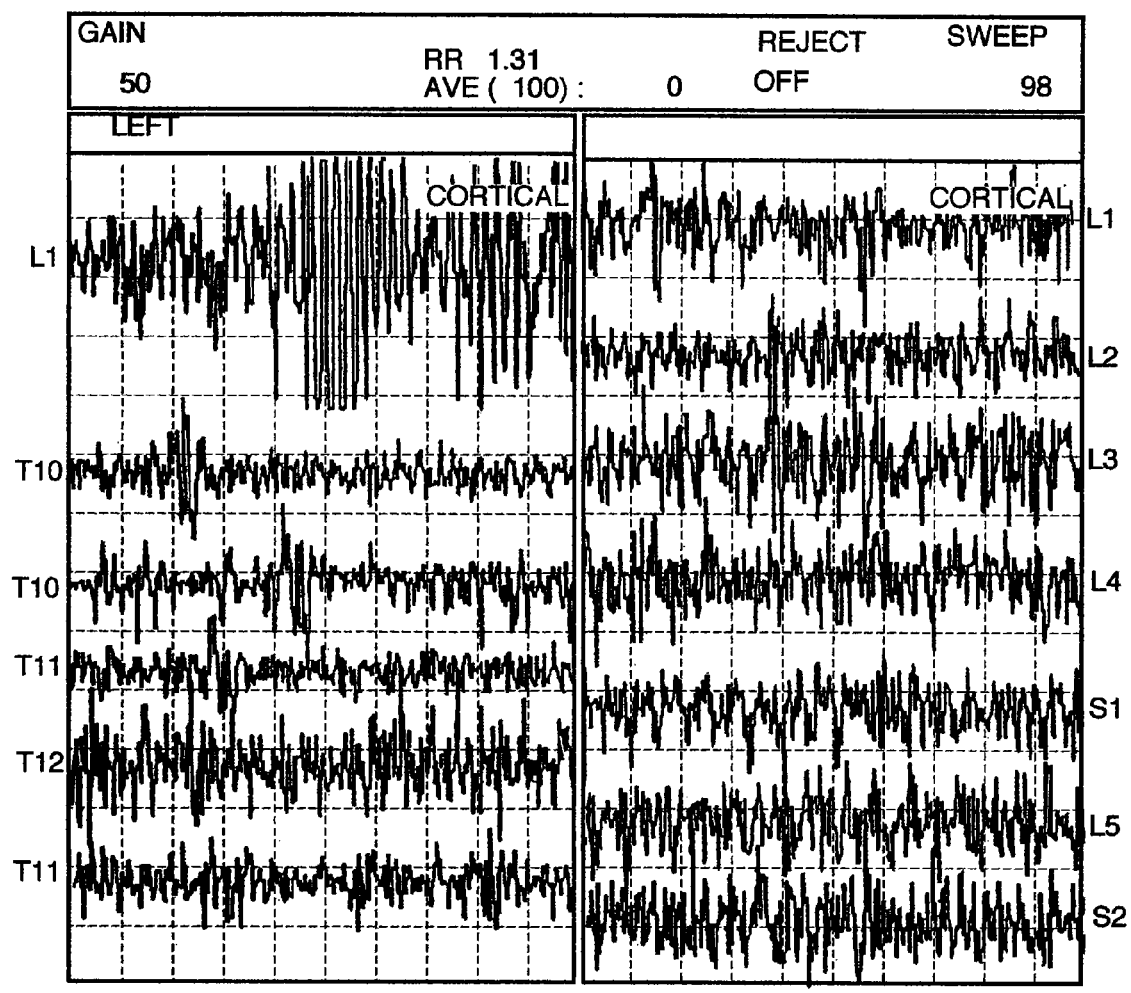
FIGS. 7A–C illustrate electrophysiological analysis performed on a quadriplegic prior to and after DREZ microcoagulation. Initial recordings on the left side, T10-S2, show both normal and aberrant neuroelectrical activity (7A); corresponding recordings after DREZ microcoagulation on L1–L5 (left panel) and recordings after second DREZ microcoagulation on L2-S1 (7B); band pass filter (65–100 Hz) on recordings of S2 DREZ prior to DREZ microcoagulation, showing greater than 3 spindles per second (7C).

As shown in FIG. 7A, aberrant or hyperactive DREZ were identified at the T12, L1, L2, L3, L4, L5, S1, and S2 DREZ(s) by measuring spontaneous neuroelectric activity (for simplicity sake, only the left side DREZ(s) are shown, although like data was obtained on the right side DREZ). The location of the "hot" DREZ confirms that DREZ caudal to a level of injury in a spinal cord can show aberrant neuroelectric activity, and that the activity causes central pain in the patient because of success in relieving the patients' pain subsequent to DREZ microcoagulation of hyperperactive DREZ(s). Additionally, classical dermatomal mapping may play a role in identifying the aberrant DREZ(s) in quadriplegic and paraplegic patients when the corresponding regions of the spinal cord have not been injured. In such cases, classical dermatomal mapping is also considered in conjunction with the somatotopic maps shown and discussed above.

Figure 7B:
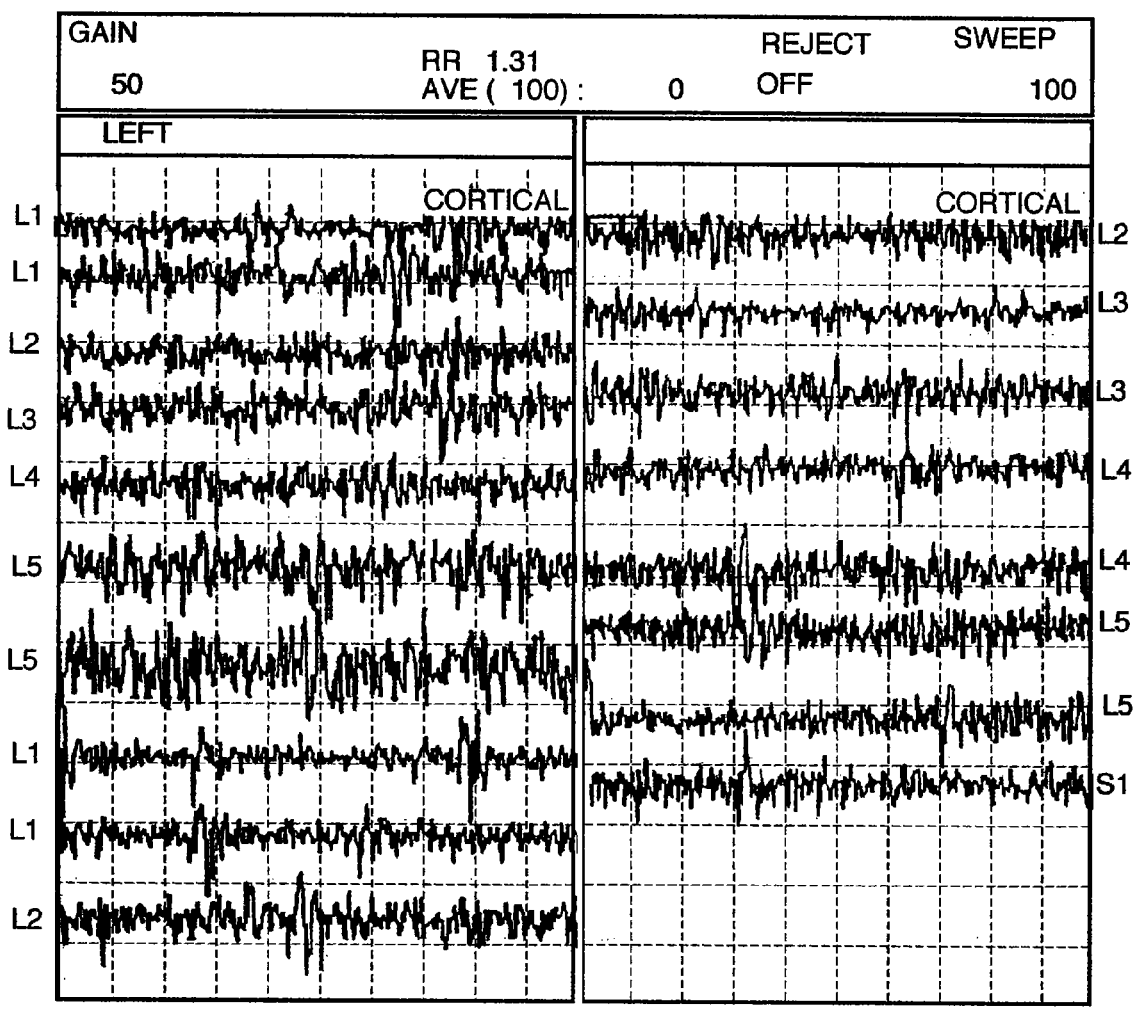
Figure 7C:
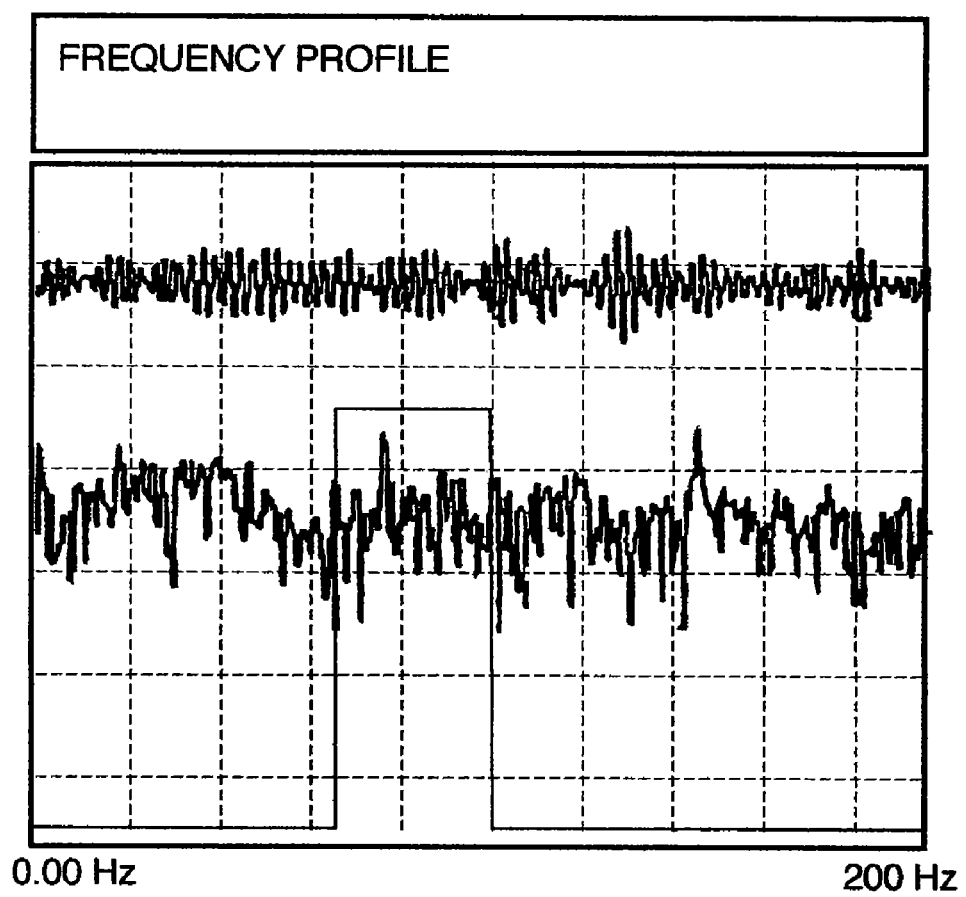

DREZ microcoagulation techniques were used to reduce the electrical activity in the "hot" DREZ, as is shown in FIG. 7B (left panel), which were repeated to reduce the electrical activity in the DREZ to even lower levels (see FIG. 7B, right panel). Finally, FIG. 7C provides spindle activity on the S2 DREZ, again confirming that a DREZ caudal to the level of injury can have the potential of being neuroelectrically active or hot. It should be noted that TCS was used to confirm the location of specific pain generating DREZ, however, the data is not shown.

Figure 8A:
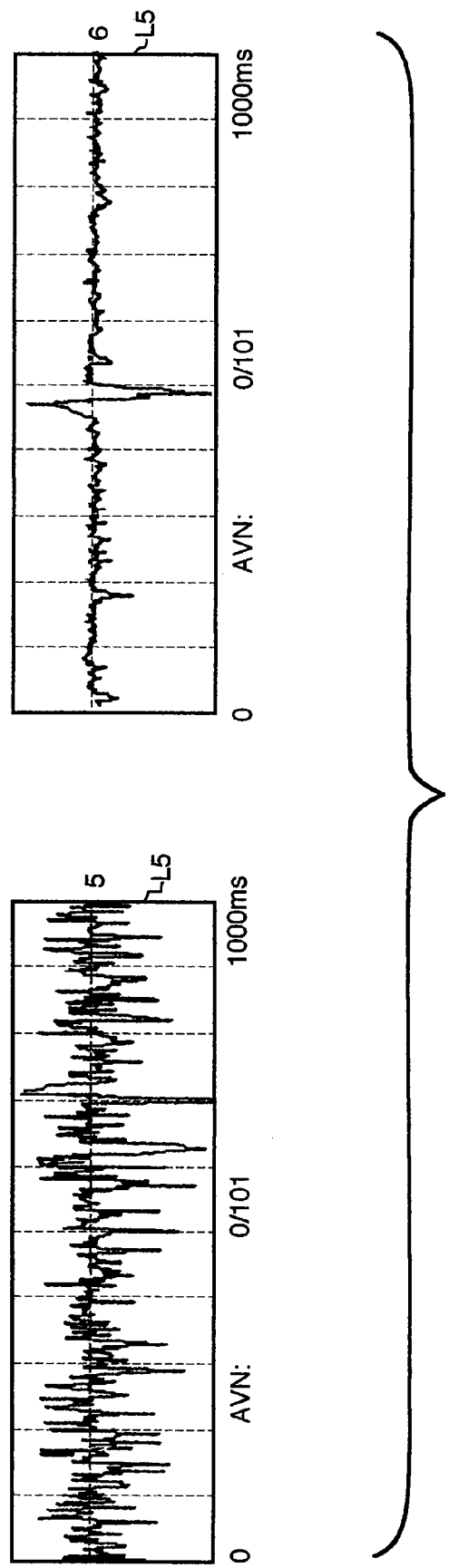
FIGS. 8A and B illustrate electrophysiological analysis performed on a paraplegic prior to and after DREZ microcoagulation. Initial recordings on the right L5 (left panel) and post DREZ microcoagulation of corresponding DREZ (right panel) (8A); band pass filter (65–100 Hz) on recordings of L5 DREZ, showing greater than 3 spindles per second (8B).
Figure 8B:
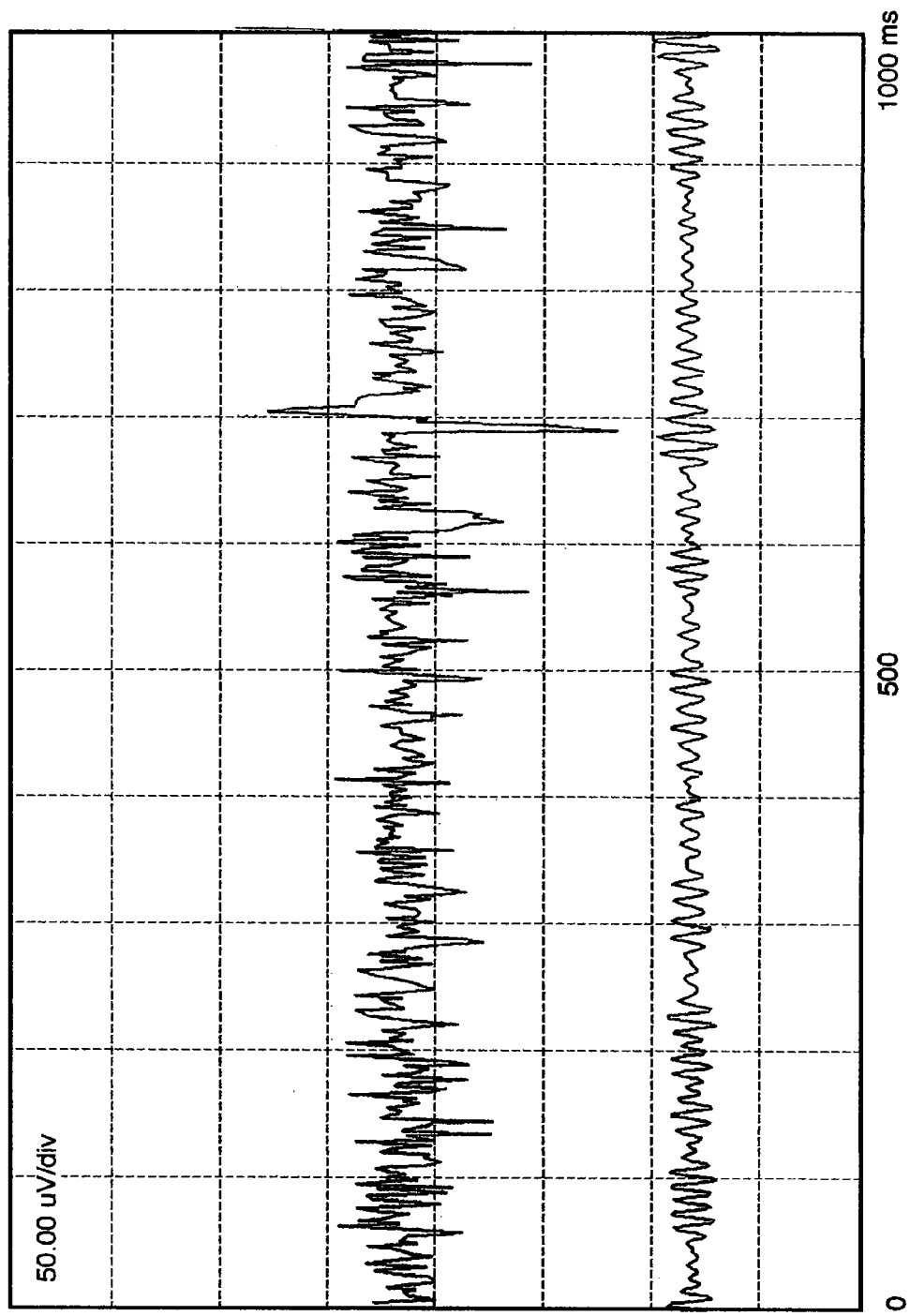

FIG. 8 provides a second illustration of a patient having below-level pain that corresponds to hyperactive or hot DREZ caudal to the level of injury (transected spinal cord), as measured by spontaneous neuroelectric activity. The patient in this case was a paraplegic having perceived pain in the legs and feet. FIG. 8A shows that the patient had a "hot" L5 DREZ (left panel), which could be ablated by DREZ microcoagulation (right panel). FIG. 8B provides the spindle activity on the L5 DREZ, again confirming that DREZ caudal to the level of injury can be neuroelectrically active.

The invention has been described with reference to specific examples. These examples are not meant to limit the invention in any way. It is understood for purposes of this disclosure, that various changes and modifications may be made to the invention that are well within the scope of the invention. Numerous other changes may be made which will readily suggest themselves to those skilled in the art and which are encompassed in the spirit of the invention disclosed herein and as defined in the appended claims.

This specification contains numerous citations to publications and patents. Each is hereby incorporated by reference for all purposes.

What is claimed is:

1. A method for minimizing central pain in a patient having a spinal cord injury, the method comprising:
    determining the level of injury in the patient;
    determining the location of perceived central pain in the patient;
    mapping the location of the perceived pain in the patient to a potential pain generating DREZ of the patient's spinal cord, the mapping consistent with a pre-determined somatotopic map, wherein the somatotopic map provides a standard guide for a DREZ location that correlates to a perceived central pain, as previously determined from a series of test subjects having spinal cord injuries; and
    surgically exposing and causing one or more lesions in the identified pain generating DREZ, wherein the one or more lesions minimizes central pain in the patient and wherein each lesion in the pain generating DREZ site(s) is introduced by radio-frequency microcoagulation at about 90 degree C. for 30 seconds.

2. The method of claim 1 wherein any two lesions in the target DREZ sites are separated by about one millimeter.

* * * * *